United States Patent
Korkuch et al.

(10) Patent No.: US 11,793,977 B2
(45) Date of Patent: Oct. 24, 2023

(54) PEEL-AWAY SHEATH ASSEMBLY

(71) Applicant: Abiomed, Inc., Danvers, MA (US)

(72) Inventors: Christopher Nason Korkuch, Danvers, MA (US); Glen Fantuzzi, Danvers, MA (US); Drew Calabrese, Danvers, MA (US); Clifford Liu, Danvers, MA (US); John Modlish, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 161 days.

(21) Appl. No.: 16/414,474

(22) Filed: May 16, 2019

(65) Prior Publication Data
US 2019/0351194 A1  Nov. 21, 2019

Related U.S. Application Data

(60) Provisional application No. 62/802,454, filed on Feb. 7, 2019, provisional application No. 62/672,212, filed on May 16, 2018.

(51) Int. Cl.
*A61M 25/06* (2006.01)
*A61M 39/02* (2006.01)
(Continued)

(52) U.S. Cl.
CPC ...... *A61M 25/0668* (2013.01); *A61M 25/005* (2013.01); *A61M 25/0045* (2013.01);
(Continued)

(58) Field of Classification Search
CPC ............. A61M 25/0668; A61M 39/02; A61M 2025/0675; A61M 60/135;
(Continued)

(56) References Cited

U.S. PATENT DOCUMENTS 4,317,445 A  3/1982  Robinson
4,380,252 A  4/1983  Gray et al.
(Continued)

FOREIGN PATENT DOCUMENTS

CN  104623790 A  5/2015
EP  0077827 A1  5/1983
(Continued)

OTHER PUBLICATIONS

Partial International Search Report, PCT/US2019/032736, dated Aug. 12, 2019 (2 pages).
(Continued)

*Primary Examiner* — Shefali D Patel
(74) *Attorney, Agent, or Firm* — Botos Churchill IP Law LLP

(57) ABSTRACT

Systems and methods for a multi-layered peel-away sheath assembly for insertion of a blood pump, the peel-away sheath assembly including a sheath hub and a sheath body having a proximal end that is connected to the sheath hub, and a distal end. The sheath body comprises multiple layers including a reinforcing layer. The reinforcing layer improves flexibility and kink resistance of the assembly. The reinforcing layer can comprise LCP, PEBAX, stainless steel, Nitinol, or Kevlar. The reinforcing layer may be a laser-cut hypotube or a braided or coiled filament. A first layer material and a third layer material are thermoplastics, including PEBAX or TPU. The reinforcing layer has at least one discontinuity, which is aligned with peel-away lines in the sheath body to allow an operator to peel-away the assembly. The peel-away lines are formed of inner notches, outer notches, or both inner notches and outer notches. The sheath hub also includes a discontinuity to allow the sheath hub to peel-away.

12 Claims, 24 Drawing Sheets

(51) Int. Cl.
*A61M 60/13* (2021.01)
*A61M 25/00* (2006.01)
*A61M 60/857* (2021.01)
*A61M 60/165* (2021.01)
*A61M 25/01* (2006.01)
*A61M 39/10* (2006.01)

(52) U.S. Cl.
CPC ........ *A61M 25/0097* (2013.01); *A61M 39/02* (2013.01); *A61M 60/13* (2021.01); *A61M 60/165* (2021.01); *A61M 60/857* (2021.01); *A61M 2025/0188* (2013.01); *A61M 2025/0675* (2013.01); *A61M 2039/1061* (2013.01)

(58) Field of Classification Search
CPC .......... A61M 25/0012; A61M 25/0009; A61M 25/005; A61M 25/0045; A61M 2025/0188; A61M 2039/1061; A61M 25/0052; A61M 25/0097; A61M 39/08; A61M 39/10; A61M 60/13; A61M 25/0051; A61M 25/007; A61M 2025/006
See application file for complete search history.

(56) References Cited

U.S. PATENT DOCUMENTS

| | | |
|---|---|---|
| 4,402,685 A | 9/1983 | Buhler et al. |
| 4,569,347 A | 2/1986 | Frisbie |
| 4,651,751 A | 3/1987 | Swendson et al. |
| 4,699,611 A | 10/1987 | Bowden |
| 4,798,594 A | 1/1989 | Hillstead |
| 4,895,565 A | 1/1990 | Hillstead |
| 5,069,674 A | 12/1991 | Fearnot et al. |
| 5,139,486 A | 8/1992 | Moss |
| 5,180,372 A | 1/1993 | Vegoe et al. |
| 5,221,255 A | 6/1993 | Mahurkar et al. |
| 5,234,425 A | 8/1993 | Fogarty et al. |
| 5,250,033 A | 10/1993 | Evans et al. |
| 5,279,596 A | 1/1994 | Castaneda et al. |
| 5,304,142 A | 4/1994 | Liebl et al. |
| 5,312,355 A | 5/1994 | Lee |
| 5,320,611 A | 6/1994 | Bonutti et al. |
| 5,380,304 A | 1/1995 | Parker |
| 5,395,341 A | 3/1995 | Slater |
| 5,397,310 A | 3/1995 | Chu et al. |
| 5,397,311 A | 3/1995 | Walker et al. |
| 5,405,338 A | 4/1995 | Kranys |
| 5,407,430 A | 4/1995 | Peters |
| 5,409,463 A | 4/1995 | Thomas et al. |
| 5,409,469 A | 4/1995 | Schaerf |
| 5,488,960 A | 2/1996 | Toner |
| 5,492,530 A | 2/1996 | Fischell et al. |
| 5,536,255 A | 7/1996 | Moss |
| 5,573,517 A | 11/1996 | Bonutti et al. |
| 5,599,326 A | 2/1997 | Carter |
| 5,653,697 A | 8/1997 | Quiachon et al. |
| 5,713,867 A | 2/1998 | Morris |
| 5,752,937 A | 5/1998 | Otten et al. |
| 5,795,341 A | 8/1998 | Samson |
| 5,827,242 A | 10/1998 | Follmer et al. |
| 5,911,702 A | 6/1999 | Romley et al. |
| 5,935,122 A | 8/1999 | Fourkas et al. |
| 5,971,993 A | 10/1999 | Hussein et al. |
| 6,042,578 A | 3/2000 | Dinh et al. |
| 6,068,622 A | 5/2000 | Sater et al. |
| 6,165,163 A | 12/2000 | Chien et al. |
| 6,197,014 B1 | 3/2001 | Samson et al. |
| 6,197,016 B1 | 3/2001 | Fourkas et al. |
| 6,217,565 B1 | 4/2001 | Cohen |
| 6,258,080 B1 | 7/2001 | Samson |
| 6,290,692 B1 | 9/2001 | Klima et al. |
| 6,319,244 B2 | 11/2001 | Suresh et al. |
| 6,338,730 B1 | 1/2002 | Bonutti et al. |
| 6,363,273 B1 | 3/2002 | Mastrorio et al. |
| 6,379,346 B1 | 4/2002 | McIvor et al. |
| 6,423,052 B1 | 7/2002 | Escano |
| 6,428,556 B1 | 8/2002 | Chin |
| 6,454,744 B1 | 9/2002 | Spohn et al. |
| 6,508,966 B1 | 1/2003 | Castro et al. |
| 6,544,270 B1 | 4/2003 | Zhang |
| 6,562,049 B1 | 5/2003 | Norlander et al. |
| 6,589,227 B2 | 7/2003 | Sønderskov Klint |
| 6,613,038 B2 | 9/2003 | Bonutti et al. |
| 6,652,508 B2 | 11/2003 | Griffin et al. |
| 6,692,462 B2 | 2/2004 | Mackenzie et al. |
| 6,702,972 B1 | 3/2004 | Markle |
| 6,740,073 B1 | 5/2004 | Saville |
| 6,749,600 B1 | 6/2004 | Levy |
| 6,814,715 B2 | 11/2004 | Bonutti et al. |
| 6,824,553 B1 | 11/2004 | Samson et al. |
| 6,827,710 B1 | 12/2004 | Mooney et al. |
| 6,852,261 B2 | 2/2005 | Benjamin |
| 6,866,660 B2 | 3/2005 | Garabedian et al. |
| 6,881,211 B2 | 4/2005 | Schweikert et al. |
| 6,887,417 B1 | 5/2005 | Gawreluk et al. |
| 6,939,327 B2 | 9/2005 | Hall et al. |
| 6,939,337 B2 | 9/2005 | Parker et al. |
| 7,018,372 B2 | 3/2006 | Casey et al. |
| 7,025,746 B2 | 4/2006 | Tal |
| 7,037,295 B2 | 5/2006 | Tiernan et al. |
| 7,101,353 B2 | 9/2006 | Lui et al. |
| 7,144,411 B2 | 12/2006 | Ginn et al. |
| 7,169,118 B2 | 1/2007 | Reynolds et al. |
| 7,226,433 B2 | 6/2007 | Bonnette et al. |
| 7,357,794 B2 | 4/2008 | Makower et al. |
| 7,367,967 B2 | 5/2008 | Eidenschink |
| 7,422,571 B2 | 9/2008 | Schweikert et al. |
| 7,438,712 B2 | 10/2008 | Chouinard |
| 7,497,844 B2 | 3/2009 | Spear et al. |
| 7,524,305 B2 | 4/2009 | Moyer |
| 7,540,865 B2 | 6/2009 | Griffin et al. |
| 7,628,769 B2 | 12/2009 | Grandt et al. |
| 7,637,903 B2 | 12/2009 | Lentz et al. |
| 7,645,273 B2 | 1/2010 | Lualdi |
| 7,704,245 B2 | 4/2010 | Dittman et al. |
| 7,713,260 B2 | 5/2010 | Lessard et al. |
| 7,722,567 B2 | 5/2010 | Tal |
| 7,731,694 B2 | 6/2010 | Becker et al. |
| 7,744,571 B2 | 6/2010 | Fisher et al. |
| 7,749,185 B2 | 7/2010 | Wilson et al. |
| 7,766,820 B2 | 8/2010 | Core |
| 7,833,218 B2 | 11/2010 | Lunn et al. |
| 7,837,671 B2 | 11/2010 | Eversull et al. |
| 7,871,398 B2 | 1/2011 | Chesnin et al. |
| 7,905,877 B1 | 3/2011 | Jimenez et al. |
| 7,909,798 B2 | 3/2011 | Osypka |
| 7,963,948 B2 | 6/2011 | Melsheimer |
| 7,968,038 B2 | 6/2011 | Dittman et al. |
| 7,985,213 B2 | 7/2011 | Parker |
| 7,989,042 B2 | 8/2011 | Obara et al. |
| 7,993,305 B2 | 8/2011 | Ye et al. |
| 8,021,409 B2 | 9/2011 | Aggerholm |
| 8,070,898 B2 | 12/2011 | Eversull et al. |
| 8,123,726 B2 | 2/2012 | Searfoss et al. |
| 8,147,452 B2 | 4/2012 | Nardeo et al. |
| 8,206,375 B2 | 6/2012 | Snow |
| 8,231,551 B2 | 7/2012 | Griffin et al. |
| 8,246,574 B2 | 8/2012 | Jacobs et al. |
| 8,257,298 B2 | 9/2012 | Hamboly |
| 8,273,059 B2 | 9/2012 | Nardeo et al. |
| 8,292,827 B2 | 10/2012 | Musbach et al. |
| 8,298,189 B2 | 10/2012 | Fisher et al. |
| 8,303,570 B2 | 11/2012 | Gregorich et al. |
| 8,317,754 B2 | 11/2012 | Leeflang et al. |
| 8,343,136 B2 | 1/2013 | Howat et al. |
| 8,366,720 B2 | 2/2013 | Mitelberg et al. |
| 8,377,035 B2 | 2/2013 | Zhou et al. |
| 8,398,696 B2 | 3/2013 | Buiser et al. |
| 8,475,431 B2 | 7/2013 | Howat |
| 8,529,719 B2 | 9/2013 | Pingleton et al. |
| 8,591,495 B2 | 11/2013 | Fischell et al. |
| 8,597,277 B2 | 12/2013 | Lenker et al. |
| 8,636,270 B2 | 1/2014 | Ostrovsky |

(56) References Cited

U.S. PATENT DOCUMENTS

| | | |
|---|---|---|
| 8,672,888 B2 | 3/2014 | Tal |
| 8,684,963 B2 | 4/2014 | Qiu et al. |
| 8,728,055 B2 | 5/2014 | Stehr et al. |
| 8,758,402 B2 | 6/2014 | Jenson et al. |
| 8,821,510 B2 | 9/2014 | Parker |
| 8,974,420 B2 | 3/2015 | Searfoss et al. |
| 9,095,684 B2 | 8/2015 | Martinez-Arraras |
| 9,168,359 B2 | 10/2015 | Rowe et al. |
| 9,295,809 B2 | 3/2016 | Sheetz |
| 9,320,873 B2 | 4/2016 | Okamura |
| 9,352,116 B2 | 5/2016 | Guo et al. |
| 9,427,551 B2 | 8/2016 | Leeflang et al. |
| 9,492,636 B2 | 11/2016 | Heideman et al. |
| 9,517,323 B2 | 12/2016 | Kimmel et al. |
| 9,539,368 B2 | 1/2017 | Haslinger et al. |
| 9,539,411 B2 | 1/2017 | Cully et al. |
| 9,545,496 B2 | 1/2017 | Hiroshige et al. |
| 9,597,481 B2 | 3/2017 | Ishikawa |
| 9,616,195 B2 | 4/2017 | Lippert et al. |
| 9,622,892 B2 | 4/2017 | Baker et al. |
| 9,629,978 B2 | 4/2017 | Eversull et al. |
| 9,707,373 B2 | 7/2017 | Nielsen |
| 9,884,169 B2 | 2/2018 | Bierman et al. |
| 9,901,706 B2 | 2/2018 | Storbeck et al. |
| 9,937,319 B1 | 4/2018 | Leeflang et al. |
| 9,980,710 B2 | 5/2018 | Seifert et al. |
| 9,981,115 B2 | 5/2018 | Merk et al. |
| 9,987,460 B2 | 6/2018 | Brustad et al. |
| 10,065,015 B2 | 9/2018 | Leeflang et al. |
| 10,076,639 B2 | 9/2018 | Guo et al. |
| 10,086,172 B2 | 10/2018 | Okamura |
| 10,124,151 B2 | 11/2018 | Okamura et al. |
| 2002/0058910 A1 | 5/2002 | Hermann et al. |
| 2002/0072712 A1 | 6/2002 | Nool et al. |
| 2003/0083623 A1 | 5/2003 | Berg et al. |
| 2004/0059296 A1 | 3/2004 | Godrey |
| 2004/0122360 A1 | 6/2004 | Waldhauser et al. |
| 2004/0267202 A1 | 12/2004 | Potter |
| 2004/0267203 A1 | 12/2004 | Potter et al. |
| 2005/0090802 A1 | 4/2005 | Connors et al. |
| 2005/0149105 A1 | 7/2005 | Leeflang et al. |
| 2005/0182387 A1 | 8/2005 | Webler |
| 2006/0095050 A1 | 5/2006 | Hartley et al. |
| 2006/0111614 A1 | 5/2006 | Saadat et al. |
| 2006/0135981 A1 | 6/2006 | Lenker et al. |
| 2006/0161135 A1 | 7/2006 | VanDerWoude |
| 2006/0200110 A1 | 9/2006 | Lentz et al. |
| 2006/0287574 A1 | 12/2006 | Chin |
| 2007/0167930 A1 | 7/2007 | Eversull et al. |
| 2007/0267012 A1 | 11/2007 | McCarthy |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0082165 A1 | 4/2008 | Wilson et al. |
| 2008/0306442 A1 | 12/2008 | Bardsley et al. |
| 2009/0240202 A1 | 9/2009 | Drasler et al. |
| 2010/0082000 A1 | 4/2010 | Honeck et al. |
| 2010/0228178 A1 | 9/2010 | McGraw |
| 2010/0268196 A1 | 10/2010 | Hastings et al. |
| 2010/0305509 A1 | 12/2010 | Osypka et al. |
| 2012/0245527 A1 | 9/2012 | Stephens et al. |
| 2013/0018309 A1 | 1/2013 | Ewing et al. |
| 2013/0131718 A1 | 5/2013 | Jenson et al. |
| 2013/0317438 A1 | 11/2013 | Ellingwood et al. |
| 2013/0317481 A1 | 11/2013 | Ellingwood et al. |
| 2014/0031843 A1 | 1/2014 | Rettenberg et al. |
| 2015/0051541 A1 | 2/2015 | Kanemasa et al. |
| 2015/0174364 A1 | 6/2015 | Kennelly et al. |
| 2015/0201963 A1 | 7/2015 | Snow |
| 2015/0352330 A1 | 12/2015 | Wasdyke et al. |
| 2016/0001042 A1 | 1/2016 | Worley et al. |
| 2016/0051798 A1 | 2/2016 | Weber et al. |
| 2016/0058976 A1 | 3/2016 | Okamura et al. |
| 2016/0066948 A1 | 3/2016 | Ellingwood et al. |
| 2016/0096000 A1 | 4/2016 | Mustapha |
| 2016/0220358 A1 | 8/2016 | Wilson et al. |
| 2016/0346507 A1 | 12/2016 | Jackson et al. |
| 2016/0346508 A1 | 12/2016 | Williams et al. |
| 2016/0354583 A1 | 12/2016 | Ellingwood et al. |
| 2016/0375222 A1 | 12/2016 | Wada |
| 2017/0043135 A1 | 2/2017 | Knutsson |
| 2017/0056063 A1 | 3/2017 | Ellingwood et al. |
| 2017/0072165 A1 | 3/2017 | Lim et al. |
| 2017/0087331 A1 | 3/2017 | Cully et al. |
| 2017/0113018 A1 | 4/2017 | Shimizu et al. |
| 2017/0120008 A1 | 5/2017 | Burkholz et al. |
| 2017/0238965 A1 | 8/2017 | Murphy |
| 2017/0252535 A1 | 9/2017 | Ganske et al. |
| 2017/0274179 A1 | 9/2017 | Sullivan et al. |
| 2017/0281908 A1 | 10/2017 | Ellingwood et al. |
| 2017/0296777 A1 | 10/2017 | Heisei et al. |
| 2017/0333682 A1 | 11/2017 | Nardeo |
| 2017/0340860 A1 | 11/2017 | Eberhardt et al. |
| 2018/0001061 A1 | 1/2018 | Okamura et al. |
| 2018/0015254 A1 | 1/2018 | Cragg et al. |
| 2018/0043138 A1 | 2/2018 | Chu |
| 2018/0056037 A1 | 3/2018 | Shimizu |
| 2018/0228502 A1 | 8/2018 | Shaffer et al. |
| 2018/0250498 A1 | 9/2018 | Stern et al. |
| 2018/0256847 A1 | 9/2018 | Lareau et al. |
| 2018/0344987 A1 | 12/2018 | Lancette et al. |
| 2018/0361116 A1 | 12/2018 | Quick et al. |

FOREIGN PATENT DOCUMENTS

| | | |
|---|---|---|
| EP | 0617977 A1 | 10/1994 |
| EP | 1212185 A1 | 6/2002 |
| EP | 1053039 B1 | 12/2005 |
| EP | 1631343 B1 | 11/2007 |
| EP | 1656963 B1 | 11/2007 |
| EP | 1853331 B1 | 5/2011 |
| EP | 1444000 B1 | 6/2011 |
| EP | 2335764 A1 | 6/2011 |
| EP | 2068994 B1 | 8/2012 |
| EP | 2703069 A2 | 3/2014 |
| EP | 2429628 B1 | 1/2017 |
| EP | 3132823 A1 | 2/2017 |
| EP | 3311873 A1 | 4/2018 |
| EP | 3347079 A1 | 7/2018 |
| EP | 3395301 A1 | 10/2018 |
| EP | 2473123 B1 | 1/2019 |
| GB | 2528639 A | 2/2016 |
| JP | 8257128 A | 10/1996 |
| JP | 4326702 B2 | 9/2009 |
| JP | 4695878 B2 | 6/2011 |
| JP | 5581139 B2 | 8/2014 |
| WO | WO-93/08986 | 5/1993 |
| WO | WO-93/15872 | 8/1993 |
| WO | WO-97/37713 | 10/1997 |
| WO | WO-2000/048659 | 8/2000 |
| WO | WO-2001/041858 | 6/2001 |
| WO | WO-2009/114556 | 9/2009 |
| WO | WO-2017/094697 | 6/2017 |
| WO | WO-2018/191547 | 10/2018 |

OTHER PUBLICATIONS

Invitation to Respond to Written Opinion issued by Intellectual Property Office of Singapore dated Apr. 7, 2022, 1 page.
Written Opinion issued by the Intellectual Property Office of Singapore dated Apr. 7, 2022, (6 pages).
Office Action from corresponding Indian Application No. 202017053493 dated Feb. 27, 2023 (6 pages).
Office Action issued in corresponding Japanese Patent Application No. 2020-564174 dated May 1, 2023 (12 pp.).
Office Action from corresponding Chinese Patent Application No. 2019800464558 dated Jul. 28, 2023 (18 pp.).
Office Action issued in corresponding Israeli Patent Application No. 278619 dated Aug. 17, 2023 (4 pp.).

A-A'

B-B'

PEEL-AWAY SHEATH ASSEMBLY

RELATED APPLICATION

This application claims the benefit of priority from U.S. Provisional Application Ser. No. 62/672,212 filed May 16, 2018, the content of which is incorporated as Appendix A of this application, and claims the benefit of priority from U.S. Provisional Application Ser. No. 62/802,454 filed Feb. 7, 2019, the content of which is incorporated as Appendix B of this application.

BACKGROUND

Mechanical circulatory support devices are often introduced to support the function of the heart after a patient suffers a cardiac episode. In some adaptations, a heart pump is inserted through the patient vasculature and into the heart to assist in unloading the heart. The pump may be configured to pull blood from the left ventricle of the heart and expel it into the aorta; or to pull blood from the inferior vena cava (IVC), bypass the right atrium and right ventricle, and expel blood into the pulmonary artery. Some systems operate the pump by an on-board motor, while others operate the pump with an external motor. Still other systems use an extracorporeal pump with a long cannula that reaches through the patient vasculature and into the heart. Other systems use pumps that do not go into the heart but remain in the aorta or other vessel.

A mechanical circulatory support device (e.g., an intracardiac heart pump assembly), or other medical devices, can be introduced into a patient in various ways. A common approach is to introduce through the vascular system either surgically or percutaneously during a cardiac procedure. For example, a catheterization procedure may be applied through the femoral artery using a sheath, such as a peel-away introducer sheath. In another approach, the sheath can be inserted through axillary or subclavian insertion sites. The sheath can alternatively be inserted in other locations, such as the femoral vein or any path for delivery of a pump for supporting either the left or right side of the heart.

The introducer sheath can be inserted into the femoral artery through an arteriotomy to create an insertion path for the pump assembly. A portion of the device is then advanced through an inner lumen of the introducer sheath and into the artery. Once the device (e.g., the pump assembly) has been inserted, the introducer sheath is peeled away. A repositioning sheath can then be advanced, for example, over the pump assembly and into the arteriotomy. Replacing the introducer sheath with the repositioning sheath during insertion of a medical device can reduce limb ischemia and bleeding at the insertion site in the skin (or at the insertion site within the vessel) due to the improved fixation of the repositioning sheath to the patient when used with a hemostatic valve.

Peel-away sheaths provide the advantage of creating vascular access and allowing passage of a medical device with the option of removal of the sheath through the peeling of the sheath into two sections, leaving the device indwelling. As referred to herein, a sheath can be an introducer sheath, a repositioning sheath, or any other peel-away sheath used in conjunction with a vascular device.

A flexible and kink-resistant introducer sheath is desirable because of the bending forces the sheath experiences as it is introduced along an introduction path. The path follows the sheath's axis through a surface arteriotomy, then through tissue and then into a blood vessel. The path is at an angle relative to the surface of the patient's skin at the insertion site. After reaching the blood vessel, the sheath then transitions to align with the path of the blood vessel (e.g., femoral artery). The insertion angle may vary based on the particular patient, procedure, and practitioner using the sheath. The blood vessel axis may vary depending on the patient and the portion of the vasculature into which the introducer sheath is being placed. The angle between the insertion axis and vessel axis influences the risk of sheath kinking. The angle can range from about 15 degrees to about 75 degrees, depending on the patient and procedure location. The higher this angle, the more likely an introducer sheath is to kink at the axial transition. Due to any sheath having a finite length, higher insertion angles are typically required for deeper vessels to keep a minimum desired portion of the introducer in the artery (2 cm-5 cm). Clinicians using ultrasound typically use high insertion angles to aid in visualization of the access needle, ultimately causing a high angle of insertion for the sheath. Some femoral insertions suffer from kinking with obese patients because the vessel is deeper with respect to the insertion point. Tortuosity, especially in the iliacs, can also cause a sheath to kink. In particular, percutaneous axillary insertions, compared with femoral insertions, are deeper and require higher insertion angles so as to avoid hitting nerve bundles in the adjacent areas of the axillary insertion sites. Therefore, introducer sheaths used during percutaneous axillary insertions, e.g. subclavian percutaneous axillary insertions, can be more prone to kink during insertion.

Some techniques are known to improve kink resistance, such as adding structural reinforcement, as done for example in some catheters. However, structural reinforcements are normally not compatible with peel-away functionality. Preferred reinforcing materials are generally materials with relatively high elastic moduli, or materials that can lend to the structural reinforcement relatively high stiffnesses, e.g. metals. Due to their material properties, these reinforcing materials also render peeling away of the device difficult or impossible. Polymer reinforcing layers are sometimes used as structural reinforcements, but their ability to improve kink resistance and flexibility is limited due to their inherent material properties. Polymers, and layers constructed from polymers have much lower elastic moduli and stiffnesses, respectively, than do metals, for example.

SUMMARY

The systems, methods, and devices described herein provide a flexible introducer sheath with peel-away sheath functionality that has improved resistance to kinking and improved flexibility for introducing a vascular device, such as an intracardiac blood pump system or other mechanical circulatory support device, into patient vasculature. An introducer sheath with such improved functionality can be achieved in various ways, as disclosed herein. In general, the sheath has at least two sections of differing rigidity, with one rigid section and at least one less rigid section. The improved sheath allows for improved kink resistance. One example configuration having at least one more rigid section and at least one less rigid section is a sheath with an inner layer, a second reinforcing layer, and an outer layer. One implementation provides a multi-layer sheath structure, including a reinforcing layer configured to have at least two discontinuities along its length. A practitioner can then apply a peel-away force to the sheath and split the sheath along the discontinuities of the reinforcing layer. One or more notches may be included along the sheath, which can also help peel away the sheath. The one or more notches extend from an outermost or innermost surface of the sheath body and penetrate through some of the sheath layers. Notches can be configured as a succession of discrete notches or as a continuous peel-away line along a length of the sheath. The alignment of the notches defines a peel-away line along which the practitioner peels away the sheath. At least one advantage of notches is the ability to define lines along which the sheath will peel away, and by aligning these lines with the discontinuities of the reinforcing layer, the amount of force needed to peel away the sheath can be reduced.

According to a first embodiment of the disclosure, a peel-away sheath assembly for insertion of a blood pump comprises a peel-away sheath hub and a peel-away sheath body. The peel-away sheath body has a proximal end portion, a distal end portion, and a middle portion, the proximal end portion being connected to the peel-away sheath hub. The peel-away sheath body further has an outer layer, an inner layer, and a reinforcing layer located between the inner layer and the outer layer. The outer layer defines an outer radius of the sheath, and the inner layer of the peel-away sheath body defines a sheath lumen having an inner radius. The inner layer further comprises a peel-away line. The peel-away line is configured as a radially extending notch, and the notch extends continuously in the longitudinal direction so as to form a line extending along the inner layer of the peel-away sheath body. The reinforcing layer is configured as a hypotube having two longitudinally extending c-shaped halves, forming a circumferential discontinuity. The reinforcing hypotube has a rigidity that is greater than at least one of a rigidity of the inner layer and a rigidity of the outer layer. The reinforcing hypotube extends along the middle portion of the peel-away sheath body, but does not extend into the distal end portion. The reinforcing layer may extend into the proximal end portion. Within the proximal end portion of the peel-away sheath body, the reinforcing layer extends proximally past a distal end of the peel-away sheath hub and terminates within the peel-away sheath hub. In some implementations, the reinforcing layer extends about 2 centimeters proximally past a distal end of the peel-away sheath hub. The specific longitudinal point at which the distal end of the peel-away sheath hub terminates is selected in order to lend to the peel-away sheath body a desired kink resistance and flexibility along the length of the peel-away sheath body. The distal end portion of the peel-away sheath body may comprise a tapered tip, designed to reduce trauma to the vasculature upon insertion of the peel-away sheath body into the patient.

According to another embodiment of the present disclosure, a peel-away sheath assembly includes a peel-away sheath hub and a peel-away sheath body. The peel-away sheath body has a proximal end portion that is connected to the peel-away sheath hub, and a distal end portion, together defining a first lumen extending in a longitudinal direction. In some configurations, the distal end portion and the proximal end portion comprise different materials. For example, the distal end portion may have an inner PEBAX layer, a stainless steel reinforcing layer, and a TPU outer layer. The proximal end portion may have an inner PEBAX layer and an outer TPU layer. Additionally, the inner layer materials may be different in the distal and proximal end portions. For example, the inner layer of the distal end portion may comprise PEBAX while the inner layer of the proximal end portion may comprise TPU, or vice versa. Similarly, the outer layer materials may be different in the distal and proximal end portions. For example, the outer layer of the distal end portion may comprise PEBAX while the inner layer of the proximal end portion may comprise TPU, or vice versa. In some implementations, the reinforcing layer is constructed of a different material between the distal and proximal layers. For example, the reinforcing layer may be stainless steel in the distal portion and may be Nitinol in the proximal portion. The proximal end portion can have an inner diameter that is equivalent to an inner diameter of the distal end portion.

According to another embodiment of the present disclosure, the peel-away sheath body has a proximal end portion, a middle portion containing a reinforcing layer, and a distal end portion. The proximal end portion is connected to the peel-away sheath hub. The proximal end portion, middle portion, and distal end portion define a first lumen extending in a longitudinal direction. In some implementations, the reinforcing layer does not extend into the proximal end portion, and does not extend into the distal end portion. For example, the distal end portion comprises an inner polymer layer and an outer polymer layer, the middle portion comprises an inner polymer layer, a reinforcing layer, and an outer polymer layer, and the proximal end portion comprises an inner polymer layer and an outer polymer layer. For example, the distal end portion may comprise an inner PEBAX layer and an outer TPU layer, the middle portion may comprise an inner PEBAX layer, a stainless steel reinforcing layer, and an outer TPU layer, and the outer proximal end portion may comprise an inner PEBAX layer and an outer TPU layer. In some implementations, the stainless steel comprises SAE 304 stainless steel. In further implementations, the PEBAX layer comprises at least one of PEBAX 3533-7233. In some implementations, the reinforcing layer extends into the proximal end portion. In other implementations, the reinforcing layer extends into the distal end portion. In some implementations, the reinforcing layer extends into both the distal and proximal end portions. In some implementations, the inner diameter of the peel-away sheath body is substantially constant throughout its length. In other implementations, a proximal end portion of the peel-away sheath body can have an outer diameter that is less than an outer diameter of a distal end portion. One advantage of a configuration having a proximal end portion with a decreased outer diameter is that an operator may apply a smaller force to break the peel-away sheath hub, as there is less material to break through.

In some configurations, the peel-away sheath body comprises an inner layer located at an inner radius, an outer layer located at an outer radius, and a reinforcing layer located at a radius between the inner radius and the outer radius. In certain implementations, there is a hydrophilic coating over at least a portion of the outer layer. In some implementations, the portion of the outer layer over which the hydrophilic coating is placed extends from the distal end of the peel-away sheath body to between about 5 centimeters and about 2 centimeters distal of the proximal end of the peel-away sheath body. In other implementations, the portion of the outer layer over which the hydrophilic coating is placed extends from the distal end of the peel-away sheath body to between about 4 centimeters and about 3 centimeters distal of the proximal end of the sheath body. In further implementations, the portion of the outer layer over which the hydrophilic coating is placed extends from the distal end of the peel-away sheath body to about 3.5 centimeters distal of the proximal end of the peel-away sheath body. The hydrophilic coating facilitates the insertion of the peel-away sheath body into the vasculature of a patient. As coating the entire length of the peel-away sheath body with the hydrophilic coating can cause the peel-away sheath body to be dislodged from the aorta due to the arterial pressure acting on the peel-away sheath body, the proximal end portion of the peel-away sheath body is generally configured to lack the hydrophilic coating.

In some configurations, the distal and proximal end portions may comprise the same materials in the same layers. For example, the inner layer of both the distal end portion and the proximal end portion may comprise PEBAX, while the outer layer of both the distal end portion and the proximal end portion may comprise TPU. In further implementations, the middle portion comprises different materials than do the distal end portion and the proximal end portion. In some implementations, there is only a reinforcing layer in the middle portion of the peel-away sheath body, while there is no reinforcing layer in the distal and proximal end portions of the peel-away sheath body. For example, the distal and proximal end portions may have an inner PEBAX layer and an outer TPU layer, while the middle portion may have an inner PEBAX layer, a stainless steel reinforcing layer, and an outer TPU layer. One advantage of a configuration having a reinforcing layer only in the middle portion of the peel-away sheath body is the relative ease of manufacture compared to configurations having a reinforcing layer throughout the entire length of the peel-away sheath body. The absence of a reinforcing layer in the distal end portion of the peel-away sheath body allows for easier formation of a tapered distal tip, as the absence of the reinforcing layer allows the inner and outer layers to reflow. The reflow of the polymer layers provides the peel-away sheath body with an increased ability to accommodate stresses while the peel-away sheath body is bent upon introduction to or navigation through the vasculature of a patient. The reflow process may generally be controlled by melting the materials at different temperatures and by implementing different process set points. Additionally, the absence of a reinforcing layer in the proximal end portion of the peel-away sheath body helps to stabilize the injection molding process, allowing the polymer layers of the peel-away sheath body to mold to the peel-away sheath hub with consistent properties.

A length of the peel-away sheath body through which the reinforcing layer extends can be adjusted in order to prevent kinking along certain portions of the peel-away sheath body. For example, in some implementations, the reinforcing layer is absent in the distal end portion while it is present in the middle portion. In such implementations, the reinforcing layer may extend over a variable length of the proximal end portion of the peel-away sheath body. For example, the proximal end of the reinforcing layer may terminate at the same longitudinal point at which the distal end of the sheath hub terminates. In other implementations, the reinforcing layer may extend proximally past a distal end of the peel-away sheath hub. In some implementations, the reinforcing layer extends about 2 centimeters proximally past the distal end of the peel-away sheath hub. In other implementations, the reinforcing layer extends about 1 centimeter proximally past the distal end of the peel-away sheath hub. The specific point at which the reinforcing layer terminates can be selected to adjusted the kink resistance of the sheath body along the length of the peel-away sheath body. The distal end portion of the peel-away sheath body may comprise a tapered tip, designed to reduce trauma to the vasculature upon insertion of the peel-away sheath body into the patient.

The reinforcing layer has material properties that advantageously lend to the peel-away sheath assembly improved kink resistance. For example, one such physical property of the reinforcing layer is its rigidity, which is greater than a rigidity of the inner or outer layers. Stiffness is defined herein as the property of a material, measured for example by Young's Modulus or an elastic modulus, whereas rigidity is defined herein as the ability of an element (e.g. a sheath) to resist deformation. As an example, the elastic modulus of the reinforcing layer is the elastic modulus of the material of the reinforcing layer, which is higher than an elastic modulus of the materials of the inner or outer layer materials. In some implementations, the stiffness of the reinforcing layer material is greater than the that of either the inner or outer layer materials. In some configurations, the stiffness of the reinforcing layer material is between about 18 and about 12,000 times that of either the inner or outer layer materials. In other configurations, the stiffness of the reinforcing layer material is between about 100 and about 9,000 times that of the inner or outer layer materials. In other implementations, the stiffness of the reinforcing layer materials is between about 75 and about 100 times that of the inner or outer layer materials. In further implementations, the stiffness of the reinforcing layer material is between about 400 and about 500 times that of the inner or outer layer materials. In certain configurations, the stiffness of the reinforcing layer material is between about 1,000 and about 7,000 times that of the inner out outer layer materials. In further configurations, the stiffness of the reinforcing layer material is about 4,000 times that of either the inner or outer layer materials. In some implementations, the selected geometry and thickness of the reinforcing layer, along with the thicknesses of the inner and outer layers, can cause variations in the relative rigidities of the reinforcing, inner, and outer layers.

In some configurations, a material of the reinforcing layer can be LCP, PEBAX, stainless steel, Nitinol, or Kevlar. The inner layer material and the outer layer material are thermoplastics. For example, the inner layer material and the outer layer material can be PEBAX or TPU. The thickness of the inner layer can be between about 0.001 inches and about 0.015 inches. Further, the thickness of the outer layer can be between about 0.001 inches and about 0.015 inches. The total wall thickness of the implementation is less than or equal to about 0.016 inches.

The reinforcing layer advantageously provides kink resistance while also enabling the peel-away functionality of the peel-away sheath assembly. The reinforcing layer includes at least two discontinuities on its surface. For example, the discontinuities are slits or openings in the surface of the reinforcing layer. Different configurations of the slits or openings can be applied along the surface of the reinforcing layer to adjust the flexibility and kink resistance of the peel-away sheath assembly. In some implementations, at least two discontinuities are oriented in a direction perpendicular to the longitudinal axis of the peel-away sheath body on the reinforcing layer surface. This alignment advantageously creates a line along a length of the peel-away sheath body that is structurally weaker than the remainder of the peel-away sheath body, requiring less force to peel-away the peel-away sheath assembly along this line.

In some implementations, the reinforcing layer is a hypotube. The hypotube is laser cut and electropolished to dull any sharp edges left by the laser-cutting. The laser cutting leaves at least two discontinuities along the surface of the hypotube. In other implementations, the reinforcing layer is a braided filament or a coiled filament. In these implementations, the braid or coil is inherently configured with discontinuities along its surface. In further implementations, the hypotube is configured in two c-shaped halves that extend longitudinally along a length of the sheath body.

The length of discontinuities in the reinforcing layer is sized along the circumference of the sheath to balance different mechanical properties of the sheath. The circumferential length of the discontinuities must be large enough to allow notch manufacture. For example, the discontinuities must be large enough to accommodate one of the mandrel protrusions so the notch can be manufactured. At the same time, that circumferential length of the discontinuity must be small enough such that the sheath resists buckling or kinking during insertion. As such, there is a critical size of the circumferential discontinuities, also called a critical gap width, as only within a range of discontinuity length does the sheath retain all of the above advantageous properties. In some implementations, the critical gap width may range between about 0.1 and about 1.5 millimeters.

In further implementations, a series of discontinuities is configured along the surface of the reinforcing layer. In some implementations, the discontinuities are parallel to each other. In some implementations, the discontinuities lie at varying angles with respect to the surface of the reinforcing layer, such that the discontinuities are not parallel or evenly spaced. In some implementations, each discontinuity has the same length along the circumference of the sheath. Alternatively, discontinuities can have a variable length along the circumference of the peel-away sheath body. In some implementations, the discontinuities are evenly spaced along a length of the peel-away sheath body. In other examples, the discontinuities are variably spaced along the length of the reinforcing layer, to vary properties of the peel-away sheath assembly along a length of the peel-away sheath body. For example, the distance between two consecutive discontinuities may be smaller in the proximal end portion of the peel-away sheath body, such that the proximal end portion of the peel-away sheath body has a higher flexibility relative to the distal end portion of the peel-away sheath body. In other examples, the distance between the two consecutive discontinuities may be larger in the proximal and distal end portions of the peel-away sheath body, and smaller towards the middle of the length of the peel-away sheath body. In such examples, the distal and proximal end portions of the peel-away sheath body have increased kink resistance relative to the middle of the length of the peel-away sheath body, and the middle of the length of the peel-away sheath body has increased flexibility relative to the distal and proximal end portions of the peel-away sheath body. In other examples, the discontinuities lie on the surface of the reinforcing layer at an angle, such that the surface cross-section of the sheath passing through the slit is elliptical. Varying discontinuity configurations along the surface of the reinforcing layer lend to the sheath different flexibilities and kink resistances. Additionally, different discontinuity configurations can accommodate different peel-away lines on the peel-away sheath body.

The discontinuities may comprise a first set and a second set of discontinuities, wherein each discontinuity in each set of discontinuities has a center. The centers of the first set of discontinuities define a first discontinuity axis, and the centers of the second set of discontinuities define a second discontinuity axis. The first discontinuity axis and the second discontinuity axis may be offset by an angle along the circumference of the reinforcing layer. The angle by which the first and second discontinuity axes are offset may range from about 0 degrees to about 180 degrees. In some configurations, the discontinuities can be slits that extended along a circumference of the reinforcing layer. Depending on the number of discontinuities at a given longitudinal location on the sheath, the reinforcing layer comprises a plurality of arc-shaped segments separated by discontinuities. In certain implementations, the arc-shaped segments are two c-shaped halves.

In addition to the circumferential discontinuities, the reinforcing layer may have a series of openings extending around the circumference of the reinforcing layer. The openings may be circular, elliptical, rhomboidal, or, generally, any other shape that allows for the reflow of the inner and outer layers through the openings. The openings may form a ring around the circumference of the reinforcing layer at a fixed longitudinal point. In some implementations, there is a ring of openings around the circumference of the hypotube at regular intervals along the length of the hypotube. For example, there may be a ring of openings every 1.2 inches along the length of the reinforcing layer. In other implementations, the ring of openings may extend around the circumference of the reinforcing layer every 0.6 inches along the length of the reinforcing layer. In certain implementations, the ring of openings may extend around the circumference of the reinforcing layer every 0.75 inches along the length of the reinforcing layer. In further implementations, the ring of openings may extend around the circumference of the reinforcing layer every 1.05 inches along the length of the reinforcing layer. In other implementations, the ring of openings may extend around the circumference of the reinforcing layer every 0.9 inches along the length of the reinforcing layer. Each opening in each ring of openings may have a range of surface areas. For example, in some implementations, each opening has a surface area of between about 5 and about 25 square millimeters. In other implementations, the surface area of each opening is between about 10 and about 20 square millimeters. In certain implementations, the surface area of each opening is about 15 square millimeters. At least one advantage of the incorporation of the circumferentially extending series of openings along the length of the reinforcing layer allows reflow of the inner and outer layers through the openings, providing greater adherence of the inner and outer layers to each other.

As noted above, the reinforcing layer can be formed of a hypotube, a braided filament, or a coiled filament. In one implementation where the reinforcing layer is formed of a braided filament, the braided filament has a flat cross-section with a height between about 0.0005 inches and about 0.007 inches and a width between about 0.005 inches and about 0.060 inches. The braided filament can alternatively have a round cross-section with a diameter between about 0.0005 inches and about 0.007 inches. The braided filament can comprise multiple strands, and the braided filament can have a picks-per-inch (PPI) between about 7 and about 60. In another implementation where the reinforcing layer is formed of a coiled filament, the coiled filament has a flat cross-section with a height between about 0.0005 inches and about 0.007 inches and a width between about 0.005 inches and about 0.060 inches. The coiled filament can alternatively have a round cross-section with a diameter between about 0.0005 inches and about 0.007 inches. The coiled filament can comprise multiple strands, and the coiled filament can have a wraps-per-inch (WPI) of about 16 to about 75. At least one advantage of a reinforcing layer formed of a coiled or braided filament is the presence of gaps between each wrap or weave of the filament, which (similar to discontinuities of a hypotube reinforcing layer) reduces the amount of force needed to peel-away the reinforcing layer and the sheath as a whole. Further, larger gaps between each wrap or weave of the filament allow for greater sheath flexibility. At least one advantage of the braided or coiled filament is the ability to adjust a size of the gaps, i.e. select a wraps-perinch, or a size of the gaps between the braid filaments, for different applications while being able to use the same manufacturing process for the reinforcing layer.

The rigidity or flexibility of the peel-away sheath assembly may be adjusted based on the incorporation of the reinforcing layer in all or some parts of the peel-away sheath body. In some implementations, the reinforcing layer comprises circumferential discontinuities, which may be slits or openings, along its surface. For example, in some implementations, there is no reinforcing layer in a portion of the peel-away sheath body but, instead, the peel-away sheath body relies on partial reinforcement in select areas along its length for its kink resistance. Some implementations have a less rigid distal sheath (e.g., with no distal reinforcing layer) with a more rigid proximal or mid sheath (e.g., with a reinforcing layer). Other implementations have a less rigid proximal sheath (e.g., with no proximal reinforcing layer) with a more rigid distal or mid sheath (e.g., with a reinforcing layer). For example, the distal end portion of the peel-away sheath body may be designed with no reinforcing layer while the proximal or middle sections would have a reinforcing layer. At least one advantage of the absence of a reinforcing layer in the distal section of the peel-away sheath body is that it allows for the easier formation of a tapered tip, as the inner and outer layers can reflow more easily without the inclusion of the reinforcing layer. In other examples, the proximal end portion has three layers including a reinforcing layer, while the distal end portion has only an inner layer of a first layer material and an outer layer of an outer layer material. The inner layer material and the outer layer material can be at least one of PEBAX or TPU. In some implementations where the distal end portion lacks a reinforcing layer, the inner layer and the outer layer comprise the same inner and outer material. However, the inner and outer layers can also be of different materials. For example, the inner layer can be PEBAX and the outer layer can be TPU. In other implementations, there is no reinforcing layer in the proximal end portion of the sheath but it is included in the middle, distal end portion, or both. In further implementations, there is no reinforcing layer in a middle portion of the sheath, but such a layer is included in the proximal end portion, distal end portion or both. In further implementations, the reinforcing layer is present in alternating segments of the sheath. At least one advantage of a partial reinforcing layer is that the sheath can have different rigidities along its length, e.g., in its proximal and distal end portions, to help with sheath insertion. For example, a lower rigidity in the distal end portion advantageously minimizes trauma to the vasculature. As another example, a higher rigidity in the proximal end portion advantageously preserves kink resistance for the peel-away sheath body by varying the rigidity. Varying the stiffness of the materials of the layers of the peel-away sheath body, and in turn varying the rigidity of portions of the peel-away sheath body can change the rigidity of the peel-away sheath assembly as a whole, for example to facilitate kink resistance.

As discussed previously, a length of the peel-away sheath body through which the reinforcing layer extends can be adjusted in order to prevent kinking along certain portions of the peel-away sheath assembly. For example, in some implementations, the reinforcing layer is absent in the distal end portion while it is present in the middle portion. In such implementations, the reinforcing layer may extend into the proximal end portion over a variable length. For example, the proximal end of the reinforcing layer may terminate at the same longitudinal point at which the sheath hub terminates. In other implementations, the proximal end of the reinforcing layer may extend proximally of the distal end of the peel-away sheath hub. For example, the reinforcing layer may terminate between about 0 centimeters proximal and about 2 centimeters proximal the distal end of the peel-away sheath hub. The specific distance between the point at which the reinforcing layer terminates and the point at which the peel-away sheath hub terminates can be selected to yield a specific kink resistance between those two points along the length of the peel-away sheath body.

The kink-resistant peel-away sheath body is also configured to have a peel-away line extending along its length, the peel-away line being aligned with one or more discontinuities in the reinforcing layer of the peel-away sheath body. Alignment can be achieved longitudinally along the peel-away sheath body, for example, by positioning the discontinuity at the same circumferential position as the peel-away line. Aligning the peel-away line of the peel-away sheath body with the at least one circumferential discontinuity in the reinforcing layer allows the peel-away sheath body to be more easily peeled away. In some adaptations, the peel-away sheath body peels away without breaking through the reinforcing layer along the entire length of the peel-away sheath body. For example, in implementations having a reinforcing layer only in the distal end portion of the peel-away sheath body, the operator initiates the removal of the peel-away sheath assembly in the proximal end portion by breaking through the inner and outer layers. In implementations having a reinforcing layer only in the proximal end portion of the peel-away sheath body, the operator initiates the removal of the sheath in the proximal end portion by breaking through the reinforcing layer, and then breaks through only the inner and outer layers while separating the distal end portion of the peel-away sheath body.

The peel-away sheath hub is configured to provide handles for the operator to hold the peel-away sheath assembly. Additionally, the operator initiates the peeling-away of the peel-away sheath assembly from the peel-away sheath hub. In some designs, the peel-away sheath hub has a proximal conical portion and a distal cylindrical portion. The proximal conical portion may have a proximal discontinuity, and the distal cylindrical portion may have a distal discontinuity. In some implementations, the first and second discontinuities are circumferential discontinuities. The discontinuities are aligned with each other, and the distal end of the distal circumferential discontinuity abuts a proximal end of the at least one peel-away line extending along the length of the peel-away sheath body. At least one advantage of this alignment is to facilitate the removal of the peel-away hub along with the peel-away sheath body by reducing the force required to peel-away the peel-away sheath assembly, thereby ensuring that the operator need not break through the reinforcing layer.

In further implementations, the distal end portion of the peel-away sheath assembly is configured to have at least a pair of diametrically opposed notches along its length, the notches extending through an inner surface or outer surface of the peel-away sheath body, providing peel-away functionality. Where a reinforcing layer is present, the notches are aligned with discontinuities of the reinforcing layer, such that at a given longitudinal point along the length of the peel-away sheath body, there is a notch located at the same circumferential position as the discontinuity. At least some advantages of alignment between the notches and the discontinuity of the reinforcing layer are the ability to define peel-away lines and to reduce the amount of force required to peel-away the peel-away sheath body, thereby allowing the operator to peel away the peel-away sheath assembly. In some adaptations the peel-away occurs without breaking through the reinforcing layer. In some implementations, the notches are inner diameter notches that extend from an innermost surface of the inner layer through the reinforcing layer. In further implementations, the inner diameter notches terminate before the outer layer. In other implementations, the inner diameter notches terminate within the outer layer. In other implementations, the notches are outer diameter notches that extend from an outermost surface of the outermost layer through the reinforcing layer. In further implementations, the outer diameter notches terminate before the inner layer. In other implementations, the outer diameter notches terminate within the inner layer. In implementations having diametrically opposed notches, the notches define a pair of diametrically opposed peel-away lines on the surface of the peel-away sheath body, where each pair of peel-away lines extends along a length of the peel-away sheath body, and the peel-away sheath assembly can be separated along the peel-away lines. In some implementations, the peel-away lines run along an inner surface of the peel-away sheath body. In other implementations, the peel-away lines run along an outer surface. Notches can help reduce the amount of force required to peel-away the peel-away sheath assembly. As mentioned above, the notches can also help align the peel-away lines with a discontinuity of the reinforcing layer, for improved peel-away functionality.

Another embodiment provides a peel-away sheath assembly for insertion of a blood pump. The peel-away sheath assembly has a peel-away sheath hub and a peel-away sheath body, the peel-away sheath body having a proximal end portion that is connected to the peel-away sheath hub, and a distal end portion. The peel-away sheath body defines a first lumen extending in a longitudinal direction. The peel-away sheath body further comprises an inner layer located at an inner radius, an outer layer located at an outer radius, and a reinforcing layer located at a radius between the inner radius and the outer radius. In certain implementations, there is a hydrophilic coating over at least a portion of the outer layer. In some implementations, the portion of the outer layer over which the hydrophilic coating is placed extends from the distal end of the peel-away sheath body to between about 5 centimeters and about 2 centimeters distal of the proximal end portion of the peel-away sheath body. In other implementations, the portion of the outer layer over which the hydrophilic coating is placed extends from the distal end of the sheath body to between about 4 centimeters and about 3 centimeters distal of the proximal end of the sheath body. In further implementations, the portion of the outer layer over which the hydrophilic coating is placed extends from the distal end of the sheath body to about 3.5 centimeters distal of the proximal end of the sheath body. The hydrophilic coating facilitates the insertion of the sheath body into the vasculature of a patient. As coating the entire length of the sheath body with the hydrophilic coating can cause the sheath body to be dislodged from the aorta due to the arterial pressure acting on the sheath body, a portion of the sheath body is generally configured to lack the hydrophilic coating. The sheath body of the present implementation further comprises at least one pair of diametrically opposed notches, which extend through at least one of the inner layer or the outer layer.

In further implementations, the diametrically opposed notches can be inner diameter notches, extending from an inner surface or the inner layer, through the reinforcing layer, and terminating before or within the outer layer. At least one advantage of inner diameter notches is their relative ease of manufacture compared to the outer diameter notches. Additionally, the notches can be outer diameter notches, extending from an outer surface of the outer layer, through the reinforcing layer, and terminating before or within the inner layer. At least one advantage of outer diameter notches is the relative ease with which they facilitate the peeling-away of the sheath compared to inner diameter notches.

The peel-away sheath body may additionally have at least one pair of diametrically opposed inner notches extending through the inner layer. In some implementations, the inner notches terminate before the outer layer. In other implementations, these notches terminate within the outer layer. The peel-away sheath body further comprises at least a pair of diametrically opposed outer notches extending through the outer layer. In some implementations, the outer notches terminate before the inner layer. In other implementations, the notches terminate within the inner layer. As mentioned above, the notches help align the peel-away lines with a discontinuity of the reinforcing layer. The specific notch configuration used, particularly whether inner or outer diameter notches are used and where along the length of the sheath each notch ends, can be selected based on the geometry of the reinforcing layer to obtain the desired peel-away sheath assembly flexibility and kink resistance In some implementations, inner notches extend along a first segment of the peel-away sheath body, and outer notches extend along a second segment of the peel-away sheath body. In some implementations, the first segment and the second segment partially overlap in a longitudinal direction. The overlapping segment may serve as a transition region between the first and second peel-away sheath body segments. In other implementations, the first segment and the second segment fully overlap in a longitudinal direction. In some implementations, the first segment corresponds to the proximal end portion of the peel-away sheath body, and the second segment corresponds to the distal end portion of the peel-away sheath body. In some implementations, the first segment extends along the entire length of the peel-away sheath body. An advantage of having inner diameter notches is that they allow for over-molding on the hub by allowing the polymer layers of the sheath body to reflow during the injection molding process without the heat transfer causing the sheath layers to melt and seal the notches. At least one advantage of the outer diameter notches is that they accommodate a large variety of reinforcing layers. At least one advantage of using outer diameter notches is an improved ease of manufacture, because outer diameter notches can be used in conjunction with different hypotube geometries, different braided filament geometries, and different coiled filament geometries. As discussed below with respect to FIG. 14, after assembly of the various layers, an operator can select a position of outer diameter notches depending on the geometry of the reinforcing layer.

Also disclosed are methods of manufacturing the claimed peel-away sheath assembly, the peel-away sheath assembly comprising a peel-away sheath body and a peel-away sheath hub. The layers of the multi-layer peel-away sheath assembly can be heat-shrunk in one step, or layer by layer. The first step of an exemplary method comprises coating a mandrel with a first layer of a first material. After coating the mandrel with the first layer, an operator heat-shrinks the first layer of the first material. In the third step, an operator coats the heat-shrunk first layer with a second layer of a reinforcing layer material. The operator then coats the second layer of the second material with an outermost third layer of a third material. The third step involves coating this heat-shrunk first layer with a second layer of a second material and an outermost third layer of a third material, where the second layer is a reinforcing layer. Finally, all the layers are heat-shrunk together, yielding the final peel-away sheath assembly. In some implementations, a PTFE heat shrink is used to heat-shrink the layers. In implementations with notches, inner notches are manufactured using a mandrel with a radial protrusion, whereas outer notches are manufactured by laser-cutting or pressing a mandrel with a radial protrusion on the outer surface of the sheath.

The peel-away sheath hub is manufactured by injection molding, wherein the peel-away sheath hub material is positioned in a mold with at least two inserts. In some implementations, the peel-away sheath hub has a proximal conical section and a distal cylindrical section. The proximal conical section and the distal cylindrical section each comprise a discontinuity, which in some implementations is a circumferential discontinuity. After the peel-away sheath hub is molded and fused to the peel-away sheath body, the inserts are removed, leaving a negative space in the shape of the inserts. The space left by the removal of the inserts creates a discontinuity along the length of the peel-away sheath hub in the longitudinal direction. The discontinuities can be aligned with one another and with the peel-away lines on the sheath body to facilitate the peeling-away of the peel-away sheath hub. The peel-away sheath hub can be fused to the peel-away sheath body with the circumferential discontinuities aligned to the peel-away lines in the peel-away sheath body.

According to an additional implementation of the present disclosure, there is provided a sheath body including a first strip of a first material, a second strip of a second material, and a lumen defined by the first strip and the second strip. The first material can have a first rigidity and the second material can have a second rigidity that is different (e.g. lower) than the first rigidity. The first strip and the second strip are oriented adjacently, for example in a helix extending from a distal end to a proximal end of the sheath body. The helical or spiral structure and the alternating first and second strips of varying rigidities improves flexibility by requiring a lower force to be applied to be able to bend the introducer sheath. It also improves kink resistance by increasing the ability of the introducer sheath to strain in the flexible sections in compression along the inner diameter of a bend radius and in tension along the outer diameter of a bend radius and by increasing the collapse strength of the diameter due to the more rigid sections. Improved flexibility and increased kink resistance are beneficial for procedures with high insertion angles, e.g. procedures using percutaneous axillary insertions.

In one implementation, the first strip and the second strip are not cut perpendicular to an orientation of the first strip and the second strip. At least one advantage of this configuration is to obtain a sheath with material properties, which are a composite of the material properties of each strip, without requiring a reinforcing coil or braid to surround the sheath. In particular, this configuration yields a sheath with composite material properties adapted to increase flexibility (e.g. bending) while minimizing kinking.

In some implementations, the first material is a polyether block amide (PEBA) or a polyethylene, and the second material is a PEBA or a thermoplastic elastomer.

In certain implementations, the first strip and the second strip have the same width. In some implementations, the widths of the first strip and the second strip are 1 mm. According to other implementations, the first strip and the second strip have different widths. In some implementations, the width of the first strip is 3 mm and the width of the second strip is 1 mm. At least one advantage of varying the widths of each of the first and second strip is to vary the composite properties of the sheath to obtain the desired rigidity and bending stiffness properties for a particular introducer sheath.

In some implementations, the sheath body includes a wall having a thickness and a first notch and a second notch in the wall. The first notch and a second notch can be axially aligned along a length of the sheath body and can be oriented opposite each other. In certain implementations, the first notch and a second notch are on an inner surface of the sheath body. According to other implementations, the first notch and a second notch are on an outer surface of the sheath body. According to certain implementations, the sheath body is bisected along the first notch and the second notch during a peel-away of the sheath body. At least one advantage of the notches is to improve the ease of peeling away the sheath body when the split line passes through both first and second strips of materials with different thicknesses.

In some implementations, the sheath body includes a tapered tip. According to certain implementations, the tapered tip includes the first material and the second material. In other implementations, the tapered tip includes only the first material. According to some implementations, the tapered tip includes only the second material.

According to a further implementation of the present disclosure, there is provided an introducer sheath for the insertion of a blood pump. The introducer sheath includes a sheath body and a sheath hub. For example, the sheath body implementation of this disclosure. The sheath body can include a first strip of a first material having a first rigidity, a second strip of a second material having a second rigidity, and a first lumen defined by the first strip and the second strip. The first rigidity can be larger than the second rigidity. The first strip and the second strip can be oriented adjacently in a helix from a distal end to a proximal end of the sheath body. The sheath hub can include proximal and distal ends defining a second lumen. The distal end of the sheath hub can be attached to the proximal end of the sheath body. The helical structure of the alternating first and second strips of varying rigidities improves both flexibility by requiring a lower force to be applied to be able to bend the introducer sheath, and strength by increasing the column strength of the introducer sheath, which is the axial force required to produce buckling. Improved flexibility and increased column strength are beneficial for procedures with high insertion angles, e.g. subclavian insertion sites.

In some implementations, the first lumen and the second lumen are in fluid communication. Various instruments can be successively inserted and withdrawn through both the first and second lumen of the sheath, leading up to placement of a device in a desired location prior to peeling away the sheath.

The sheath hub can include a hemostasis valve sized for preventing fluid from exiting the proximal end of the hub.

In some implementations, the sheath hub includes a first notch and a second notch. The first notch and the second notch can be axially aligned along a length of the sheath hub and can be oriented opposite each other. In certain implementations, the first notch and the second notch can be on an inner surface of the sheath hub. In other implementations, the first notch and the second notch can be on an outer surface of the sheath hub.

According to a further implementation of the present disclosure, there is provided a method of manufacturing a flexible introducer sheath body. The method comprises wrapping a first strip of a first material and a second strip of a second material adjacently around a mandrel, and securing the strips together (e.g. by heating) so they remain adjacent and with peel-away functionality. The method may include securing a first distal end of the first strip and a second distal end of the second strip. The method may comprise securing a first proximal end of the first strip and a second proximal end of the second strip. The method also may comprise placing a heat shrink tube over the first strip, the second strip, and the mandrel. Further, the method may comprise heating the first strip and the second strip. The method further may comprise removing the heat shrink tube. The method also may comprise removing the first strip and the second strip from the mandrel.

According to a further implementation of the present disclosure, there is provided a sheath body including a first strip of a first material, a second strip of a second material, and an inner lumen defined by distal and proximal ends of the sheath body. The first material can have a first rigidity and the second material can have a second rigidity that is different than the first rigidity. The first strip and the second strip are oriented adjacently over the inner lumen, for example in a helix extending from the distal end to the proximal end of the sheath body. The inner lumen can be made of a third material having the same or different rigidity as the first and/or second materials.

In some implementations, the sheath body includes an outer wall having a first thickness, an inner wall having a second thickness, and a first notch and a second notch in the outer wall. The first notch and a second notch can be axially aligned along a length of the sheath body and can be oriented opposite each other.

At least one advantage of the manufacturing method is the ability to form a sheath with composite material properties tailored to provide improved bending flexibility and higher kink resistance. Additionally, the manufacturing method enables production of a sheath body with smooth inner and outer surfaces.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
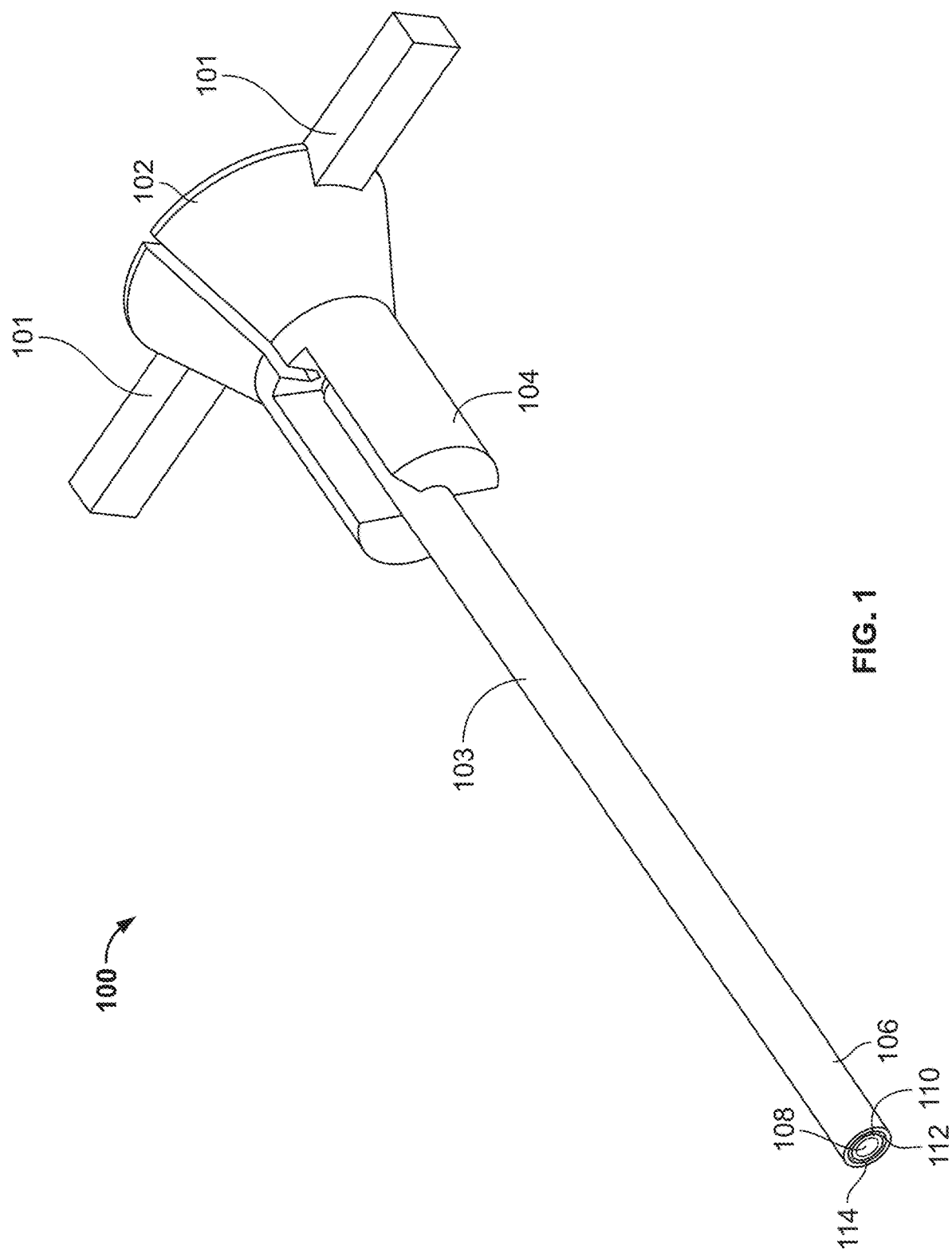
FIG. 1 shows the peel-away sheath assembly comprising the peel-away sheath body and the peel-away sheath hub.

To provide an overall understanding of the systems, method, and devices disclosed herein, certain illustrative embodiments will be described. Although the embodiments and features described herein are specifically described for use in connection with a percutaneous heart pump system, it will be understood that the teachings may be adapted and applied to other mechanical circulatory support devices and other types of medical devices such as electrophysiology study and catheter ablation devices, angioplasty and stenting devices, angiographic catheters, peripherally inserted central venous catheters, midline catheters, peripheral catheters, inferior vena cava filters, abdominal aortic aneurysm therapy devices, thrombectomy devices, TAVR delivery systems, cardiac therapy and cardiac assist devices, including balloon pumps, cardiac assist devices implanted using a surgical incision, and any other venous or arterial based endoluminal introduced catheters and devices.

The systems, methods, and devices described herein provide a flexible introducer sheath with peel-away sheath functionality that has improved resistance to kinking and improved flexibility. An introducer sheath with such improved functionality can be achieved in various ways, as disclosed herein. In general, the sheath has at least two sections of differing rigidity, with one rigid section and at least one less rigid section. The improved sheath allows for improved kink resistance. One example configuration having at least one rigid section and at least one less rigid section is a sheath with an inner layer, a second reinforcing layer, and an outer layer. In such implementations, the reinforcing layer may include a laser-cut hypotube or a braided or coiled filament. As disclosed in Application No. 62/672,212, reproduced in Appendix A below, another configuration having at least one rigid section and at least one less rigid section comprises a rigid strand and a less rigid strand wrapped in a single layer helical configuration. By making the less rigid section of the introducer sheath out of different polymer materials, the introducer sheath also allows the sheath to be peeled away easier. Using a stiffer material and a less stiff material, either in the same layer, or in different layers, is an improvement over typical peel-away sheaths that use only one material with a constant stiffness, forcing a choice between kink resistance and flexibility. Improving resistance to kinking while also improving flexibility is highly desirable in clinical scenarios requiring peel-away sheaths with high insertion angles. Such clinical scenarios include femoral access for obese patients due to the distance between the vessel and the insertion point, as well as subclavian axillary access due to sensitive anatomical landmarks and nerve bundles in the adjacent areas of the axillary insertion sites. Additionally, the presence of discontinuities in the reinforcing layer, and/or notches in the sheath layers reduces the force to be applied to peel-away the sheath.

FIG. 1 shows an illustrative peel-away sheath assembly 100 including, sheath handles 101, sheath hub 102, sheath body 103, proximal end 104, distal end 106, sheath body lumen 108, sheath body inner layer 110, reinforcing layer 112 and outer layer 114. The sheath hub 102 is coupled to the sheath body 103, sheath body 103 having a proximal end 104 and a distal end 106. The sheath hub 102 is coupled to the proximal end 104 of the sheath body 103. The sheath body 103 defines a first lumen 108, which extends along the longitudinal axis of the sheath body 103. As described further below in relation to FIGS. 2-6, peel-away sheath assembly 100 has a multi-layer design, to provide both flexibility and kink resistance. Sheath body 103 comprises an inner layer 110 located at a first and innermost radius, a reinforcing layer 112 located at a second radius, and an outer layer 114 located a third and outermost radius. The inner layer 110 and the outer layer 114 comprise a thermoplastic, which may be the same for each of inner layer 110 and outer layer 114. Alternatively, inner layer 110 and outer layer 114 may comprise different thermoplastics. The reinforcing layer 112 has different material properties than the inner layer 110 and the outer layer 114. For example, the reinforcing layer is stiffer than at least one of inner layer 110 and outer layer 114. The illustrative embodiment shown in FIG. 1 may further comprise a hydrophilic coating over at least a portion of the outer layer. In some implementations, the portion of the outer layer over which the hydrophilic coating is placed extends from the distal end of the sheath body to between about 5 centimeters and about 2 centimeters distal of the proximal end of the sheath body. In other implementations, the portion of the outer layer over which the hydrophilic coating is placed extends from the distal end of the sheath body to between about 4 centimeters and about 3 centimeters distal of the proximal end of the sheath body. In further implementations, the portion of the outer layer over which the hydrophilic coating is placed extends from the distal end of the sheath body to about 3.5 centimeters distal of the proximal end of the sheath body. As previously discussed, the hydrophilic coating facilitates the insertion of the sheath body into the vasculature of a patient. As coating the entire length of the sheath body with the hydrophilic coating can cause the sheath body to be dislodged from the aorta due to the arterial pressure acting on the sheath body, a portion of the sheath body is generally configured to lack the hydrophilic coating.

The reinforcing layer can be a hypotube, a braided filament, or a coiled filament. The reinforcing layer is configured with at least two discontinuities on its surface. For example, the hypotube of the reinforcing layer can be configured with a series of slits along its surface. Such slits allow the hypotube to not only offer improved kink resistance given its inherent rigidity, but also allow the hypotube to have improved flexibility. As another example, a braided or coiled filament second layer includes discontinuities between filament braids or wraps. At least one advantage of a filament reinforcing layer is the presence of discontinuities between each wrap or braid of the filament, which reduces the amount of force needed to peel-away the reinforcing layer and the sheath as a whole. Further, additional discontinuities between each wrap of the filament allow for greater flexibility. At least one advantage of the filament is the ability to adjust a size of the discontinuities, i.e. select a wraps-per-inch, for different applications with the same manufacturing process for the reinforcing layer. One further advantage of the filament is the ability to maintain a given size of the discontinuities while adjusting the separation between the discontinuities by varying the size of the filament. Both the filament and hypotube configurations can be implemented with a variety of peel-away line designs. One advantage of a reinforcing layer constructed from a hypotube or a coiled filament is that the thickness of the layer can be configured to be constant throughout entirety length of the layer.

The sheath body is also configured to have a peel-away line extending along its length, the peel-away line overlapping the at least one circumferential discontinuity in the reinforcing layer of the sheath. At least one advantage of the overlap between the peel-away line of the sheath and at least one circumferential discontinuity in the reinforcing layer is the ability to peel-away the sheath without having to break through the reinforcing layer.

Figure 5A:
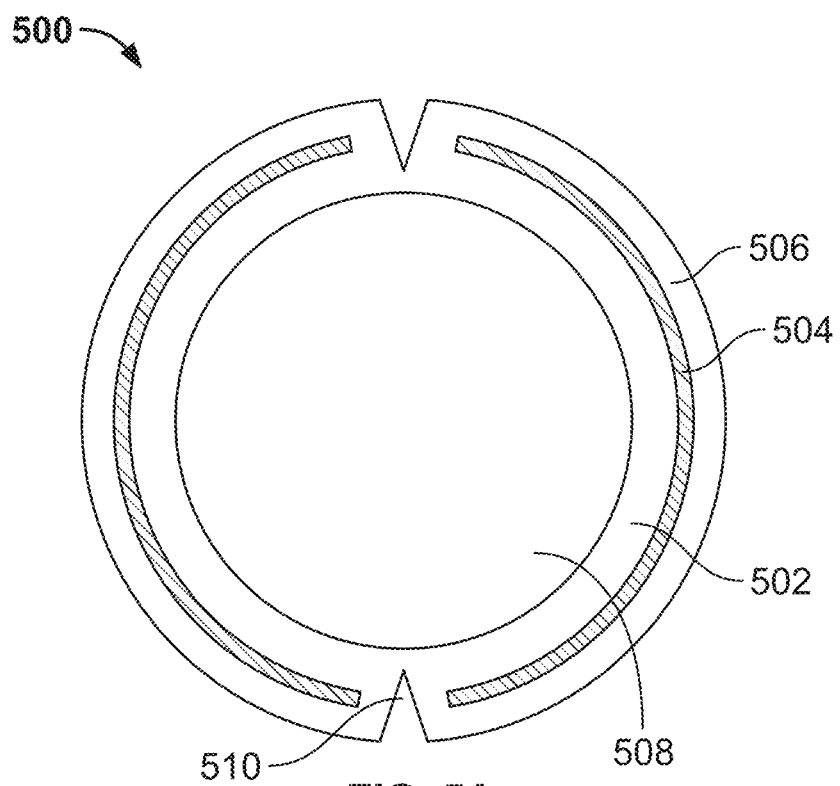
FIG. 5A-5B show possible configurations of the outer and inner diameter notches along a circumferential cross-section.
Figure 5B:
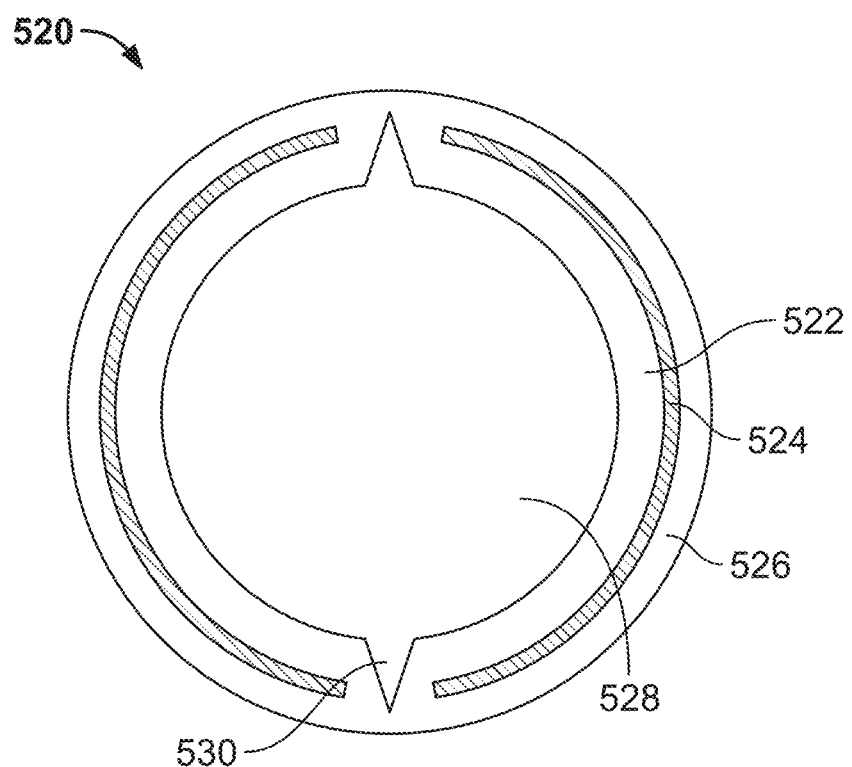

As described in relation to FIGS. 2 and 3 below, the reinforcing layer can be a laser-cut hypotube. The hypotube can be machined to have at least two discontinuities on its surface. In some implementations, the discontinuities extend along a portion of the circumference of the hypotube, and are circumferential discontinuities. In other implementations, the discontinuities extend along a length of the hypotube, and is are longitudinal discontinuities. In other implementations, the discontinuities may extend both circumferentially and longitudinally. In certain implementations, as shown for example in FIGS. 5A-B and discussed further below, representative circumferential cross-section contains several circumferential discontinuities. For example, as shown in FIG. 5A-B, the discontinuity can be two or more slits. In other implementations, the discontinuities may be of different sizes and shapes. For example, the discontinuities can be rectangular, can be circular, can be elliptical, and can be rhomboidal.

Figure 2A:
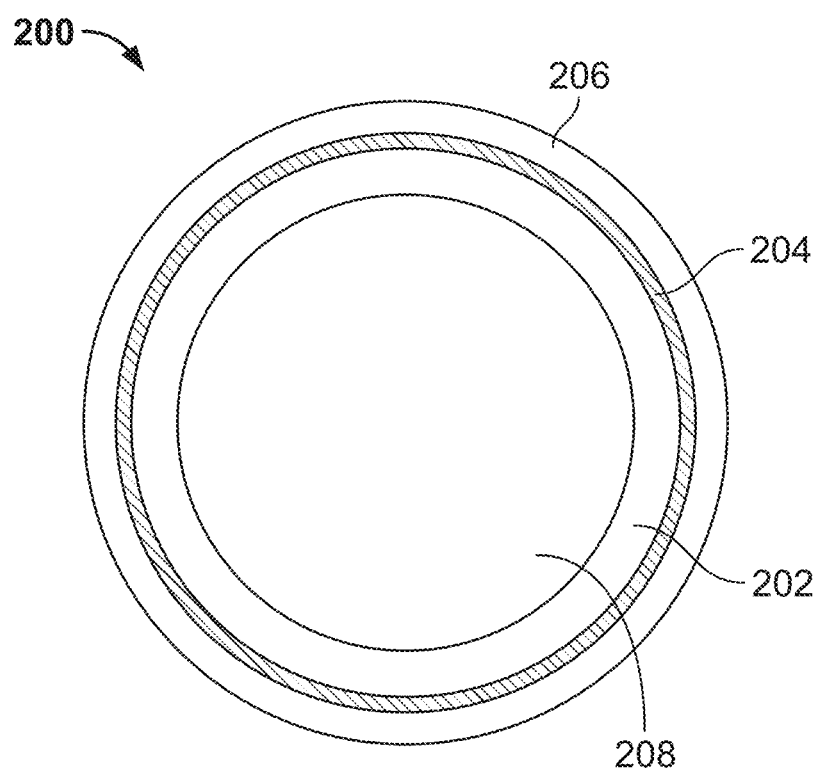
FIG. 2A shows a cross-section of the peel-away sheath body taken at a longitudinal point having a continuous second layer circumference.
Figure 3A:
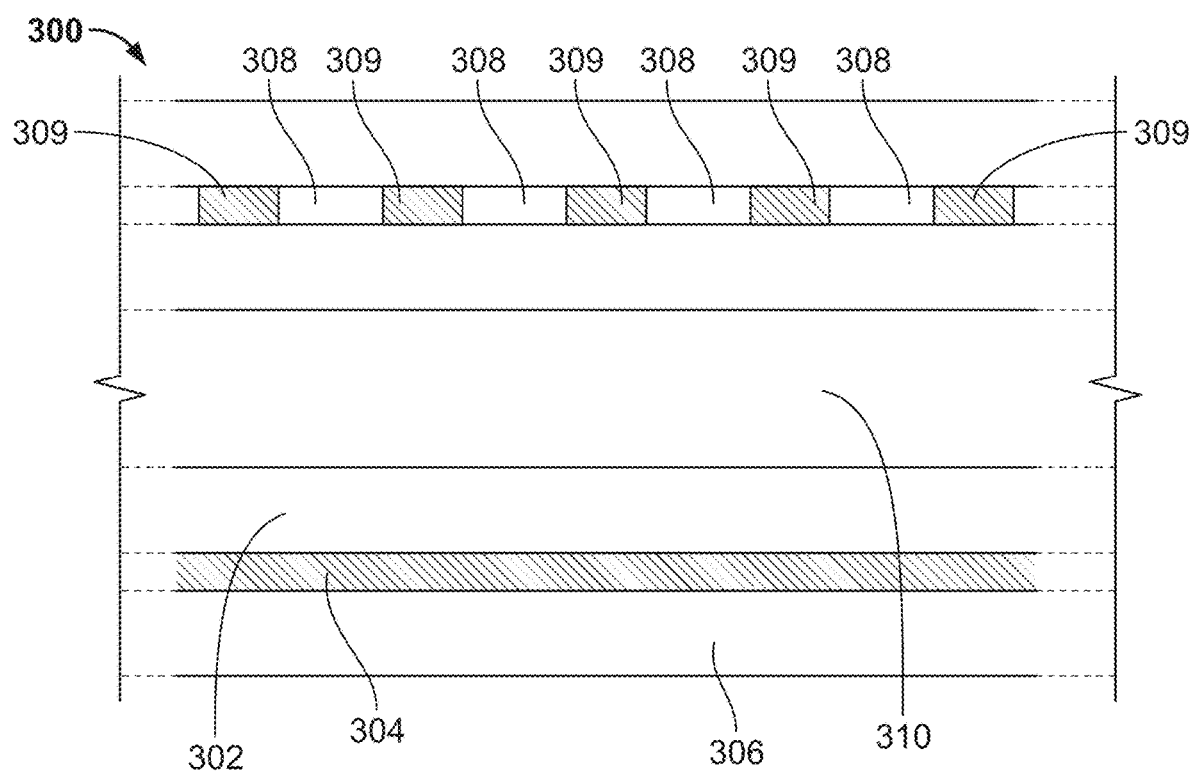
FIG. 3A shows an axial cross section of the peel-away sheath body.
Figure 3B:
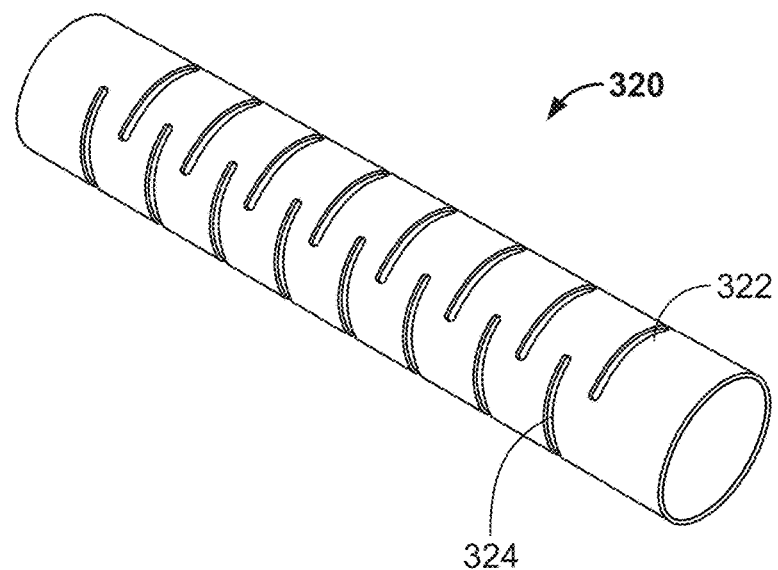
FIGS. 3B-3C show possible designs of the laser-cut hypotube.

In one implementation, as shown for example in FIG. 3B, the slits along the surface of the hypotube are parallel to each other, and are evenly spaced along the length of the hypotube. In such an implementation, there are two distinct circumferential cross-sections that may be taken along the length of the hypotube. The first circumferential cross-section is shown in FIG. 2A.

The cross-section 200 depicts inner layer 202 located at an inner radius, reinforcing layer 204 located at an intermediate radius, and outer layer 206 located at an outermost radius. The center of FIG. 2A shows first lumen 208. FIG. 2A is taken at a longitudinal point along the sheath body at which the reinforcing layer 204 has a continuous circumference. The inner layer 202, the reinforcing layer 204, and the outer layer 206 are concentric layers. Concentric, as defined herein means that the layers share the same center, with the outer layer 206 completely surrounding reinforcing layer 204 and inner layer 202, and with reinforcing layer 204 completely surrounding inner layer 202.

Figure 2B:
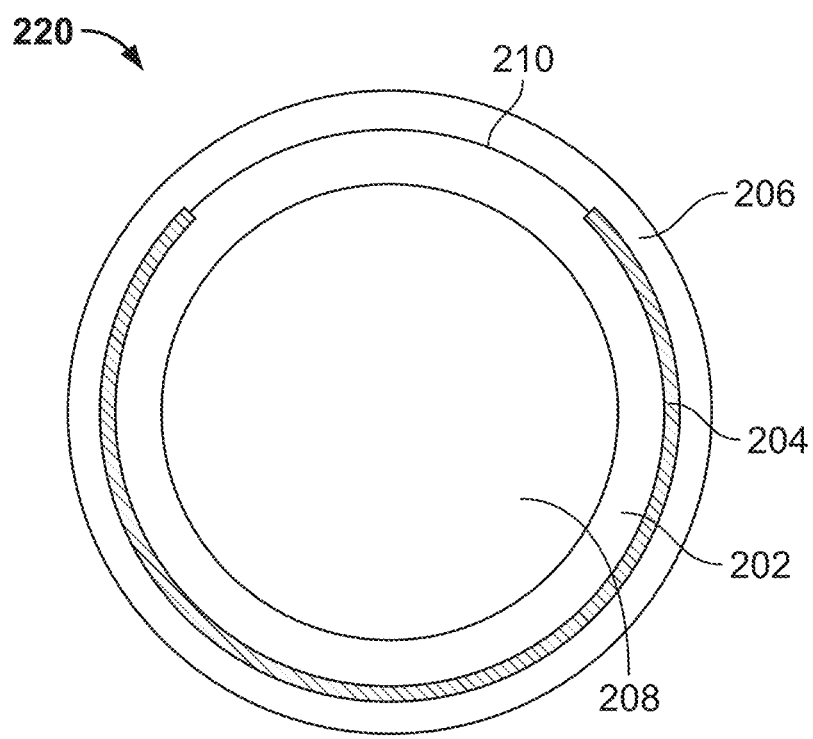
FIG. 2B shows a cross-section of the peel-away sheath body taken at a longitudinal point intersecting a circumferential discontinuity in the second layer.

The second illustrative circumferential cross-section is shown in FIG. 2B. The cross-section 220 depicts inner layer 202 located at an inner radius, reinforcing layer 224204 located at an intermediate radius, and an outer layer 226206 located at an outermost radius. The center of FIG. 2B shows first lumen 208. The cross-section of FIG. 2B is taken at a longitudinal point along the sheath body at which the reinforcing layer 204 has a circumferential discontinuity 210, corresponding to a slit in the laser-cut hypotube. As such, the cross-section of FIG. 2B shows a discontinuous reinforcing layer. The at least one circumferential discontinuity 210 defines a line that provides the sheath with its peel-away functionality.

In FIGS. 2A and 2B, the material properties of reinforcing layer 204 advantageously lend to the sheath assembly improved flexibility and kink resistance. For example, one such physical property is the rigidity of the reinforcing layer, which is greater than that of at least one of the materials of the inner layer 202 or outer layer 206. Another such physical property of the reinforcing layer material 204 is its elastic modulus, which too may be greater than at least one of those of the materials of the inner layer 202 or outer layer 206. The first inner layer 202 material and the outer layer 206 material may be a thermoplastic, and the thermoplastic can be at least one of PEBAX or TPU. The reinforcing layer 204 material can be at least one of LCP, PEBAX, stainless steel, Nitinol, or Kevlar. The thickness of the inner layer 202 can be between 0.001 inches and 0.015 inches. Further, the thickness of the outer layer 206 can be between 0.001 inches and 0.015 inches. The total wall thickness of the implementation is less than or equal to 0.016 inches.

FIG. 3A shows one illustrative longitudinal cross-section 300 of the peel-away sheath assembly, the longitudinal axis of the sheath body being in the plane of the page. The cross-section shows inner layer 302 at an inner radius, reinforcing layer 304 at an intermediate radius, and outer layer 306 at an outer radius. The reinforcing layer 304 has discontinuities 308. Discontinuities 308 are, in some implementations, circumferential discontinuities. Together, the three layers define first lumen 310. Within the reinforcing layer 304, circumferential discontinuities 308 that separate ribs 309 are connected by the reinforcing layer 304. The circumferential discontinuities 308 are of a finite arc length and do not extend along the entire length of the circumference of the reinforcing layer 304. The circumferential discontinuities 308 may be of varying arc lengths and may be of varying widths. The arc lengths of the circumferential discontinuities 308 may be between about 0.5 cm-1 cm. Similarly, the widths of the circumferential discontinuities 308 may be between about 0.1 and 0.5 cm, between about 0.2 and 0.4 cm, and about 0.3 cm.

FIG. 3B shows one configuration of discontinuities 322 and 324 in the reinforcing layer 320, in which each discontinuity 322 and 324 of the hypotube has the same length along the circumference of the hypotube. The discontinuities in FIG. 3B are evenly spaced in the longitudinal direction, and the discontinuities comprise a first set and a second set of discontinuities. The discontinuities located at the same circumferential position as first slit 322 constitute the first set, and the discontinuities located at the same circumferential position as second slit 324 define the second set. Each discontinuity in each set of discontinuities has a center. The centers of the first set of discontinuities define a first discontinuity axis, and the centers of the second set of discontinuities define a second discontinuity axis. In some embodiments, and as shown in FIG. 3B, the first and second slit axes are offset by some angle. The angle by which the two slit axes are offset may be zero degrees, such that all of the slits along the length of the hypotube are centered on the same axis. The angle by which the slit axes are offset ranges from 0 to about 180 degrees. In one example, the angle by which the slit axes are offset is 0 degrees, which corresponds to every slit being centered on the same axis. In another example, the angle by which the slit axes are offset is 180, which corresponds to the two slit axes being diametrically opposed to one another. Diametrically opposed, as defined herein means that two features of the implementation are separated along the sheath body by a 180 degree offset. In other examples, the axes may be offset by an angle between about 30 and about 150 degrees. In other examples, the axes may be offset by an angle between about 60 and about 120 degrees. In other examples, the axes may be offset by an angle of about 90 degrees. In other examples, the discontinuities have varying length along the surface of the hypotube. In other examples, the slits are variably spaced along the length of the hypotube, to achieve varying flexibility along the sheath. For example, the spacing can be fixed in the proximal portion of the sheath, and may increase in the distal direction so as to provide greater kink resistance in the distal end while providing an easier ability to peel-away in the proximal end. In another example, the slits may be closest together on both ends of the sheath body and may have greater spacing in the middle of the length of the sheath body, providing kink resistance to the middle of the sheath body while allowing for the extremities of the sheath to be easily peeled away. As described above in relation to the filament reinforcing layer, the discontinuities may be of varying sizes and shapes. Configurations having a hypotube reinforcing layer can also have discontinuities of varying shapes and sizes.

In some implementations, the hypotube may be configured to possess a spine that connects a series of ribs. A spine as defined herein refers to a portion of the hypotube that extends continuously in a longitudinal direction parallel to the first lumen of the sheath body. Ribs as herein defined refer to portions of the hypotube that are connected at only one end to the spine and extend away from the spine in a circumferential direction. In some implementations, there is only a single rib, such that the hypotube resembles a single c-shape that extends longitudinally down the length of the sheath body. In other implementations, there may be several ribs. The ribs may be separated in the longitudinal direction by circumferential discontinuities. In other implementations, there may be more than one spine, each spine being connected to a set of ribs. In all such implementations, the number of and the spacing of the ribs can be optimized to yield the desired kink resistance and flexibility. Ribs spaced closer together provide greater kink resistance. Ribs spaced farther apart provide greater flexibility and ease of peel-away.

Figure 3C:
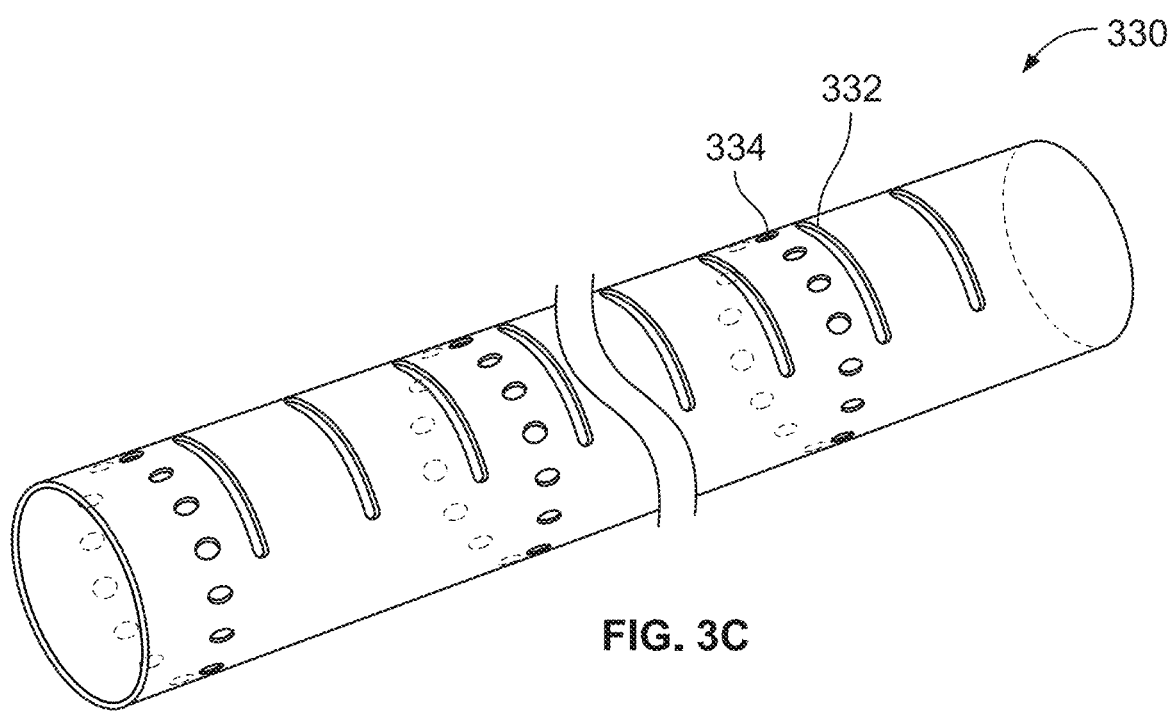

FIG. 3C shows another configuration of discontinuities 332 and openings 334 in the reinforcing layer 330. In FIG. 3C, circumferential discontinuities 332 are oriented to extend along the circumference of the reinforcing layer. The inclusion of openings 334 helps the adherence of the inner and outer layers to reinforcing layer 330 during manufacturing. Openings 334 may be configured in a variety of shapes. Openings 334, for example, may be circular, elliptical, or rhomboidal. As discussed previously, openings 334 are configured to extend along the circumference of reinforcing layer 330. Openings 334 may be oriented at regular intervals along the length of reinforcing layer 330. For example, openings 334 may be included every 0.7 inches along the length of reinforcing layer 330. In other implementations, openings 334 may be positioned every 0.9 inches along the length of the reinforcing layer. In certain implementations, openings 334 may be positioned every 1.1 inches along the length of the reinforcing layer. As previously discussed, openings 334 may have a range of surface areas. For example, in some implementations, each opening 334 has a surface area of between about 5 and about 25 square millimeters. In other implementations, the surface area of each opening 334 is between about 10 and about 20 square millimeters. In certain implementations, the surface area of each opening 334 is about 15 square millimeters. The incorporation of openings allows for the inner and the outer layer of the sheath body to better adhere to one another during manufacturing. This increased adherence allows the sheath body to better accommodate stresses while bent. The reflow process is also controlled such that there is now polymer reflow into the circumferential slits configured along the length of the hypotube. The slits remaining free of polymer allows the slits to function as compression and expansion zones, which increases the flexibility of the sheath body.

Figures 4A, 4B:
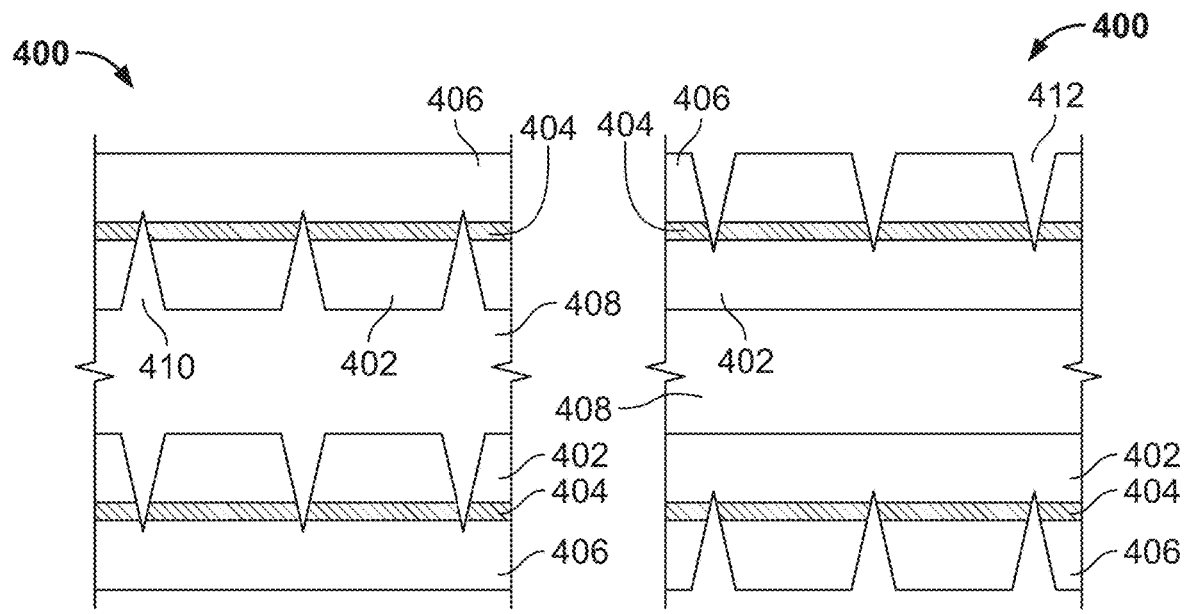
FIGS. 4A-4E show possible configurations of the inner and outer diameter notches along an axial cross-section.

FIGS. 4A-4E show several possible configurations of the inner and outer diameter notches. The notches in such configurations define a peel-away line, along which a practitioner can peel the sheath assembly to separate it. FIGS. 4A-4E show inner layer 402, reinforcing layer 404, and outer layer 406, and sheath lumen 408. Also shown is an illustrative notch 410. FIG. 4A depicts an implementation having only inner diameter notches. The inner diameter notches of FIG. 4A begin on an innermost surface of inner layer 402, penetrate through the reinforcing layer 404, and terminate within the outer layer 406. In another implementation, the outer diameter notches 410 begin on an innermost surface of inner layer 402, penetrate through the reinforcing layer 404, and terminate before the outer layer 406. Implementations containing inner diameter notches (FIG. 4A) are more easily manufactured.

FIG. 4B shows an implementation having only outer diameter notches. The outer diameter notches of FIG. 4B begin on an outermost surface of outer layer 406, penetrate through the reinforcing layer 404, and terminate within the inner layer 402. In another implementation, the outer diameter notches of FIG. 4B begin on an outermost surface of outer layer 406, penetrate through the reinforcing layer 404, and terminate before the inner layer 402. Implementations containing outer diameter notches (FIG. 4B) perform better with regard to peel-away functionality than do configurations having only inner diameter notches.

Figures 4C, 4D:
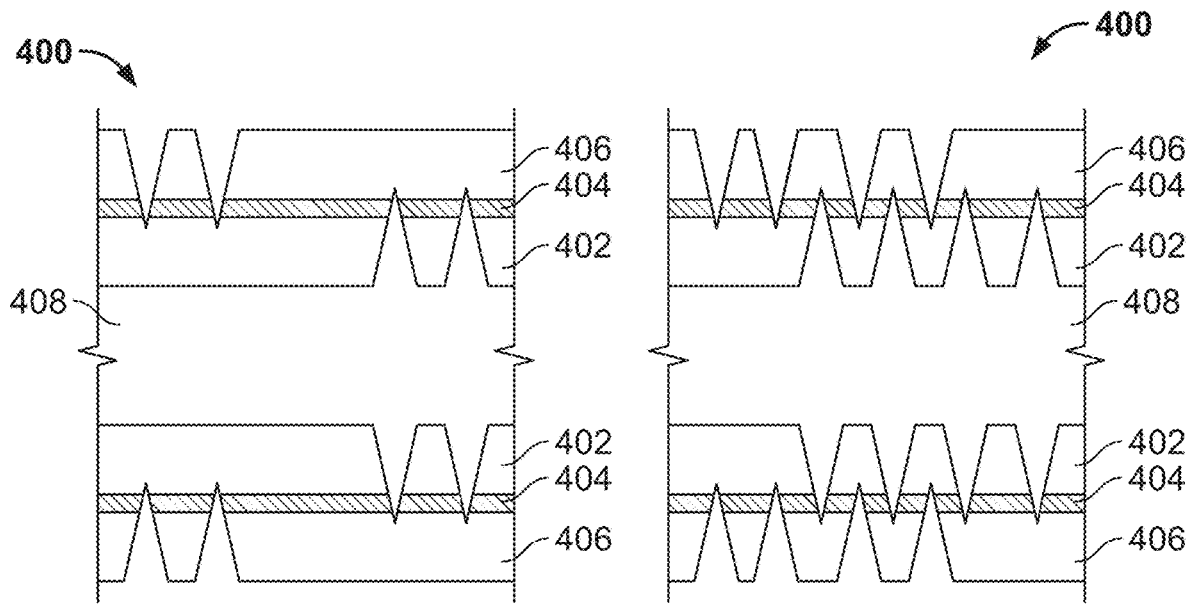
Figure 4E:
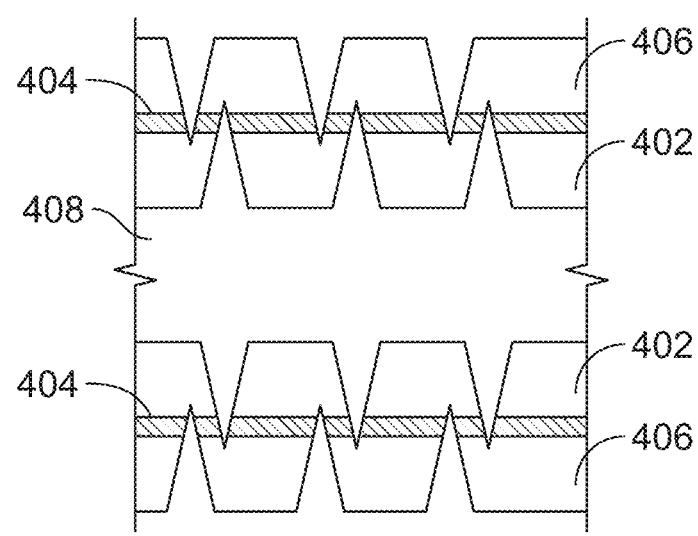

FIG. 4C shows an implementation having both inner and outer diameter notches wherein the two types of notches do not overlap longitudinally along the length of the sheath body. FIG. 4D shows an implementation wherein the notches partially overlap longitudinally along the length of the sheath body. FIG. 4E shows an implementation where the notches entirely overlap longitudinally along the length of the sheath body. In one implementation, the outer diameter notches extend along at least a distal end of the distal portion of the sheath body, and the inner diameter notches extend along all of the proximal portion of the sheath and at most a proximal end of the distal portion of the sheath body. In another implementation, the outer diameter notches extend along at least a distal end of the distal portion of the sheath body, and the inner diameter notches extend along all of the proximal portion of the sheath and at most a proximal end of the proximal portion of the sheath body in addition to both inner diameter and outer diameter notches extending overlapping along any portion of the first section of the sheath body.

FIG. 5A shows a circumferential cross-section 500 of the sheath body having inner layer 502, reinforcing layer 504, and outer layer 506. The three layers define lumen 508, which extends along the longitudinal axis of the sheath body. Diametrically opposed outer diameter notches 510 extend from an outermost surface of the outer layer 506, through the reinforcing layer 504, and terminate within the inner layer 502.

FIG. 5B shows a circumferential cross-section 520 of the sheath body having inner layer 522, reinforcing layer 524, and outer layer 526. The three layers define first lumen 528, which extends along the longitudinal axis of the sheath body. Diametrically opposed inner diameter notches 530 extend from an innermost surface of the inner layer 522, through the reinforcing layer 524, and terminate within the outer layer 526. As stated in relation to FIGS. 4A-E, the configurations having outer diameter notches, as in FIG. 5A, have improved peel-away performance, while the configurations having inner diameter notches, as in FIG. 5B, are more easily manufactured. Some implementations only have inner diameter notches, while other implementations only have outer diameter notches. Further implementations may have both inner diameter notches and outer diameter notches, wherein the inner diameter notches extended along of the length of the sheath body exclusively from the outer diameter notches. Additional implementations may have a portion of the sheath body wherein there are both inner diameter notches and outer diameter notches. Some other implementations may have both areas wherein one notch is exclusively found, and areas wherein the two types of notches are found overlapping longitudinally.

Figure 6:
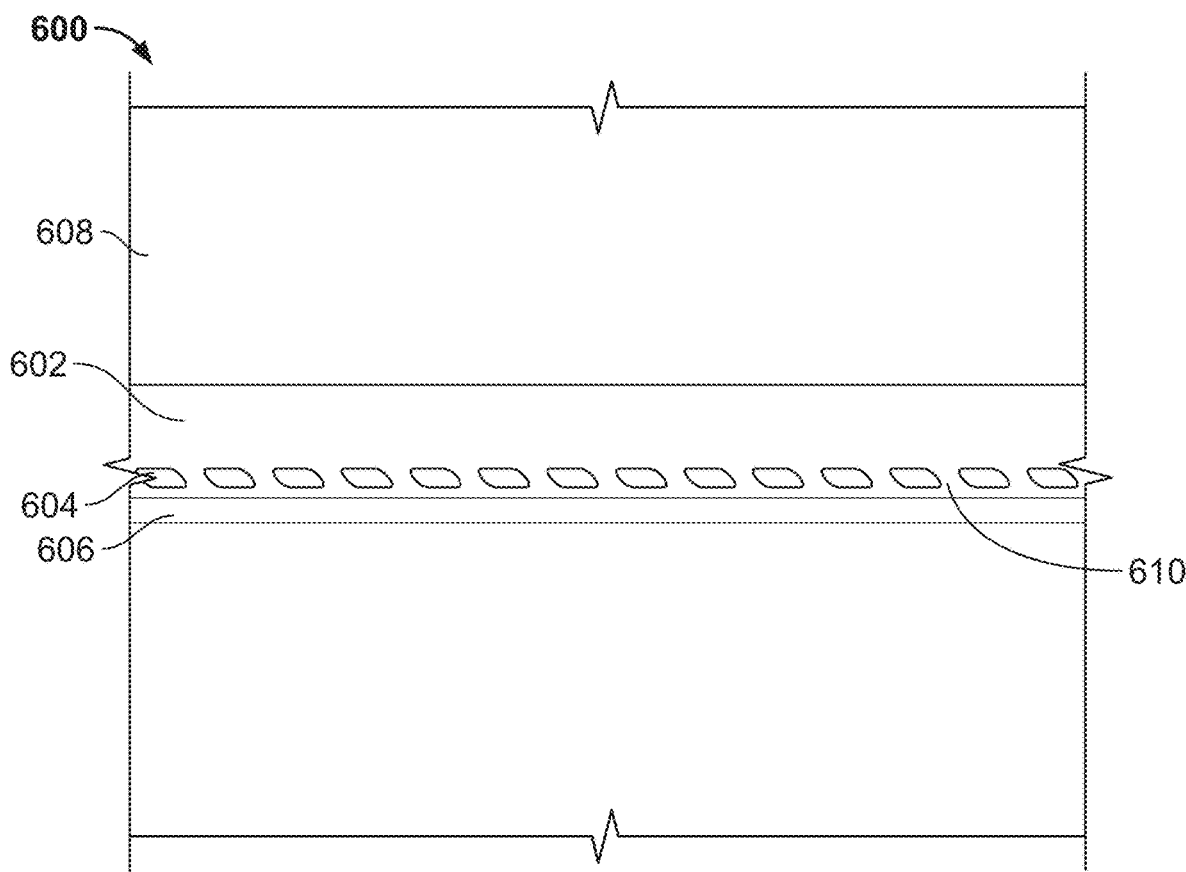
FIG. 6 shows a cross-section which shows the inner layer, the reinforcing layer, and the third layer.

FIG. 6 similarly shows a cross-section 600 of the layers of the sheath, comprising inner layer 602, reinforcing layer 604, and outer layer 606. Discontinuities 610 can be seen in reinforcing layer 604. In some implementations, discontinuities 610 are circumferential discontinuities.

Figure 7:
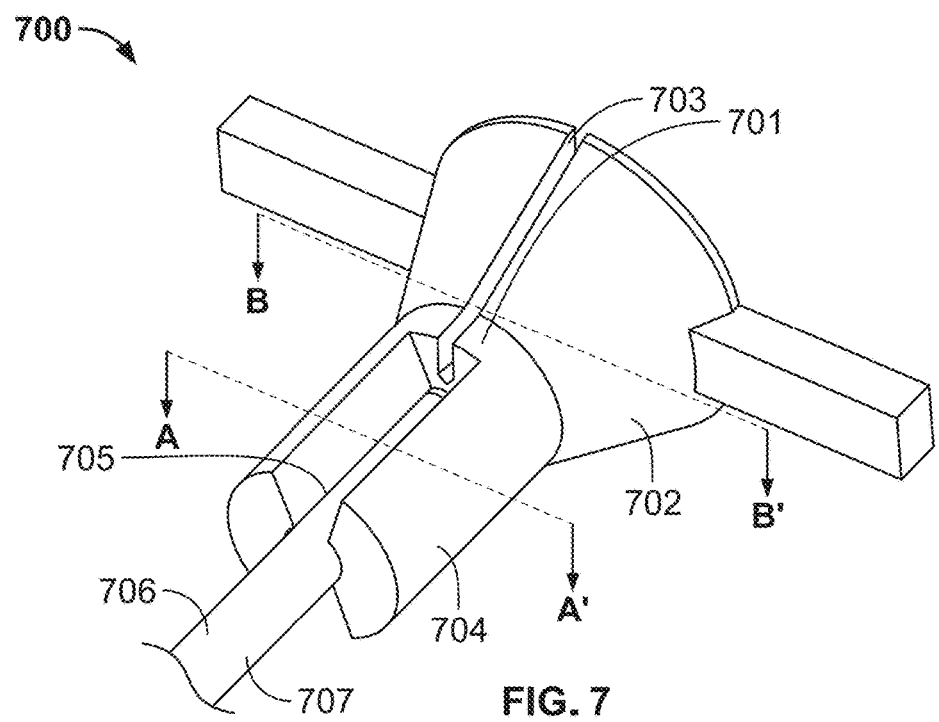
FIG. 7 shows an isometric view of the peel-away sheath hub and proximal portion of the peel-away sheath body.

FIG. 7 shows an isometric view 700 of the sheath hub 701 and the proximal portion 706 of the sheath body 707. The sheath hub comprises proximal conical proximal portion 702, having circumferential discontinuity 703, and distal conical portion 704, having circumferential discontinuity 705. Distal conical portion 704 of the sheath hub 701 is attached to proximal portion 706 of sheath body 707. The discontinuities 703 and 705 are configured to align with the peel-away lines of the sheath body 707, such that at a given longitudinal point along the length of the sheath body having a discontinuity, the peel-away line is located at the same circumferential position as the discontinuity. In some implementations, discontinuities 703 and 705 are circumferential discontinuities.

Figure 8:
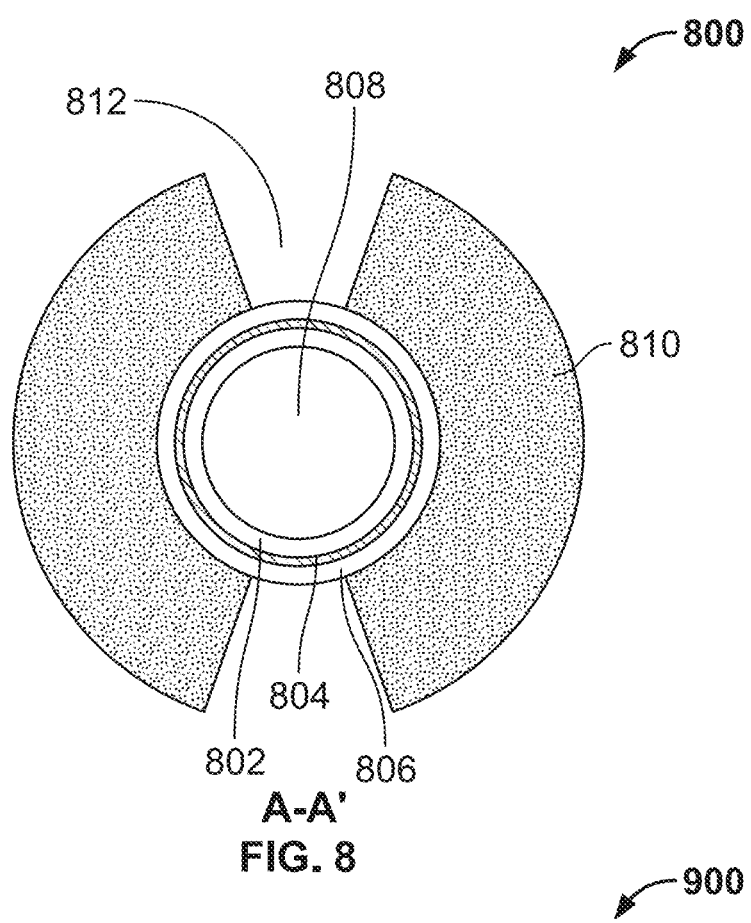
FIG. 8 shows a circumferential cross-section of the peel-away introducer sheath within the cylindrical portion of the peel-away sheath hub.

FIG. 8 shows a circumferential cross-section 800 taken along line A-A' (see FIG. 7) in the distal cylindrical portion 810 of the sheath hub. Inner layer 802, together with reinforcing layer 804, and outer layer 806 together define first lumen 808. Discontinuity 812 in the cylindrical portion 810 of the sheath hub is aligned with the peel-away lines of the sheath-body to facilitate removal of the sheath, and is, in some implementations, a circumferential discontinuity. Discontinuity 812 is aligned with the discontinuity of the proximal conical portion of the sheath hub, also to facilitate removal of the sheath. The discontinuity of the proximal conical portion of the sheath hub is, in some implementations, a circumferential discontinuity. As discussed in relation to FIG. 12, circumferential discontinuity 812 in the cylindrical portion 810 of the sheath hub is manufactured by placing an insert into the sheath hub material prior to fusing the sheath hub material to the sheath body. The insert is removed after fusion, leaving circumferential discontinuity 812 in cylindrical portion 810 of the sheath hub.

Figure 9:
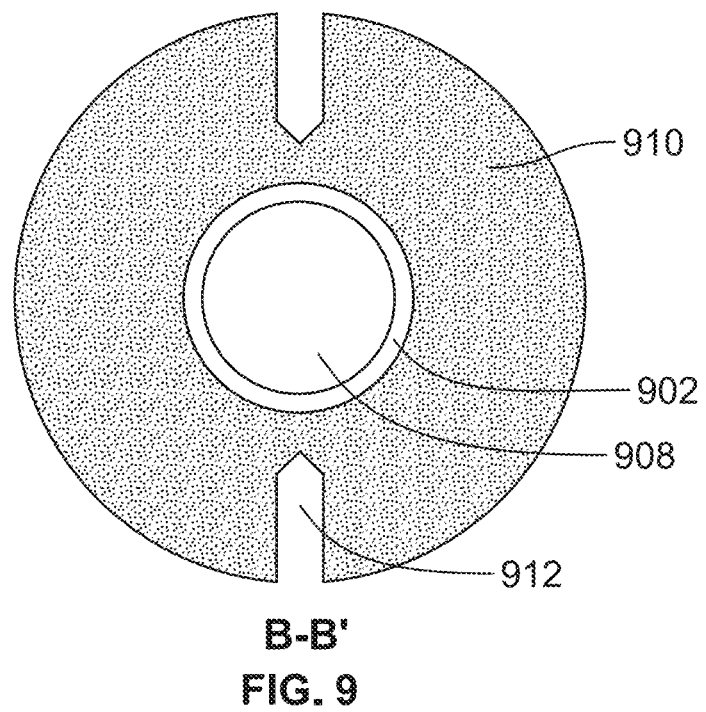
FIG. 9 shows a circumferential cross-section of the introducer peel-away sheath within the conical portion of the peel-away sheath hub.

FIG. 9 shows a circumferential cross-section 900 taken along line B-B' (see FIG. 7) in the proximal conical portion 910 of the sheath hub. Inner layer 902, defines first lumen 908. Discontinuity 912 in the conical portion 910 of the sheath hub can be aligned with the discontinuity of the distal cylindrical portion of the sheath hub to facilitate the remove of the sheath, the distal cylindrical portion of the sheath hub also being aligned with the peel-away lines of the sheath body. In some implementations, discontinuity 912 is a circumferential discontinuity. As discussed in relation to FIG. 12, and as discussed above in relation to the circumferential discontinuity in the distal cylindrical portion of the sheath hub, circumferential discontinuity 912 in the conical portion 910 of the sheath hub is manufactured by placing an insert into the sheath hub material prior to fusing the sheath hub material to the sheath body. The insert is removed after fusion, leaving circumferential discontinuity 912 in conical portion 910 of the sheath hub. Additionally, as shown in the illustrative embodiment of FIG. 9 (and discussed further in detail below in relation to FIG. 12), there exists only an inner sheath layer in the proximal conical portion of the sheath hub. As discussed below in relation to FIG. 12, inner layer 902 has a specific thickness. The thickness of inner layer 902 in proximal conical portion 910 of the sheath hub can be less than the thickness of the layers that are distal relative to proximal conical portion 910. The thickness of inner layer 902 in the proximal conical portion 910 can be selected such that there is a reduced diameter section in proximal conical portion 910. The reduced diameter section can have an outer diameter that is less than the total thickness of the relatively distal layers, or the reduced diameter section can have an outer diameter that is equal to the total thickness of the relatively distal layers. The presence of only a single sheath layer within the proximal conical portion 910 of the sheath hub decreases the amount of material through which an operator must break to separate the sheath, allowing the operator to apply a smaller breaking force.

Figure 10:
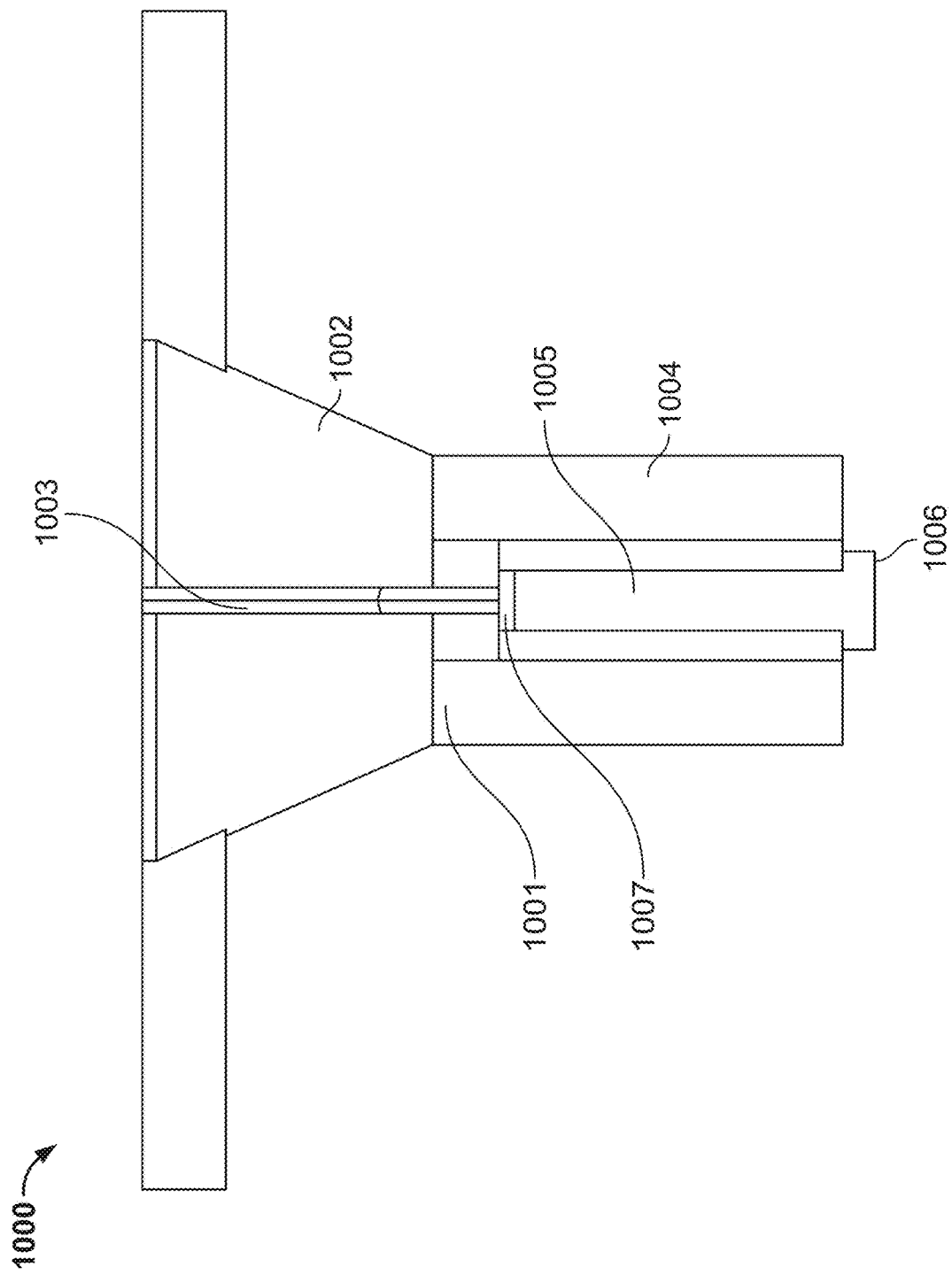
FIG. 10 shows a top view of the peel-away sheath hub and proximal end portion of the peel-away sheath body.

FIG. 10 shows a top view 1000 of the sheath hub 1001 and the proximal portion 1006 of the sheath body. Sheath hub 1001 comprises proximal conical portion 1002 and distal cylindrical portion 1004. Discontinuity 1003 resides in the conical portion 1002 of the sheath hub, and discontinuity 1005 resides in the cylindrical portion of the sheath hub. Discontinuities 1003 and 1005 are, in some implementations, circumferential discontinuities. Circumferential discontinuities 1003 and 1005 are aligned with peel-away lines on the sheath body. Proximal end 1006 of the sheath body is coupled to sheath hub 1001 at the distal conical portion 1004. FIG. 7 also shows lines A-A' and B-B', along which illustrative cross-sections of the hub in the cylindrical and conical portions, respectively, are shown in FIG. 8 and FIG. 9.

Manufacturing of the peel-away sheath includes manufacturing of the multi-layer sheath body, manufacturing of the sheath hub, and assembly of the sheath hub and sheath body. Specific notch and layer configurations can be configured for ease of manufacture. For example, the absence of a reinforcing layer in the proximal portion of the sheath helps to stabilize the injection molding process. Additionally, using inner diameter notches ensures that notches will not seal when the polymer layers reflow during the manufacturing process. As described in further detail below in relation to FIG. 14, the multi-layer sheath body is manufactured through a heat-shrinking process. Heat-shrinking is also referred to as lamination.

In one method of manufacturing, the innermost first layer material, the reinforcing second layer material, and the outermost third layer material are placed onto a mandrel. The layers are then heat-shrunk. For example, a PTFE heat shrink is used.

In another method, the innermost first layer is placed on to the mandrel and is heat-shrunk, at which point the reinforcing second layer material and the outermost third layer material are placed onto the heat-shrunk first layer. The heat-shrunk first layer, the reinforcing second layer material, and outermost third layer material are then wrapped heat-shrunk together.

In yet another method, each layer is successively heat-shrunk onto a mandrel. The innermost first layer is first placed on to the mandrel and heat-shrunk. The heat-shrunk first layer is then coated with a reinforcing second layer material. The two layers are then heat-shrunk. The two heat-shrunk layers are then coated with an outermost third layer material. The three layers are then wrapped heat-shrunk.

For manufacturing sheath bodies having inner diameter notches, the mandrel used for heat-shrinking comprises a raised spine, such that heat-shrinking of a layer using the mandrel creates a sheath body with an inner diameter notch in the shape of the mandrel spine. For manufacturing sheath bodies having outer diameter notches, the outermost third layer is configured with a mold during heat-shrinking, the mold being the shape of the outer diameter notch. Upon heat-shrinking, the mold is removed, leaving an outer diameter notch in the shape of the mold. As discussed further below in relation to FIG. 11, a circumferential discontinuity must be sufficiently large to allow for at least a mandrel through extend through the discontinuity during manufacturing and to provide improved flexibility. A size of the discontinuity cannot be smaller than a sizes of the protrusion of the mandrels used in manufacturing. However, the discontinuity must also be sufficiently small to still provide improved kink resistance—if the discontinuity is too large, the sheath will buckle.

Similar methods of manufacture exist for any configuration of the reinforcing second layer. For example, when the reinforcing layer is a hypotube comprising a plurality of hypotube arc segments, the innermost first layer may be heat-shrunk, and then the arc segments may be heat-shrunk to the heat-shrunk innermost first layer. This can be done to ensure that the increasing number of hypotube arc segments are properly adhered to the innermost first layer prior the incorporation and heat-shrinking of the outermost third layer. Additionally, when the reinforcing layer is a hypotube comprising a plurality of arc segments, the innermost first layer may be heat-shrunk, and then the arc segments may be heat-shrunk to the heat-shrunk first layer individually. Similarly, the braided and coiled filament structures previously discussed can be heat-shrunk to the heat-shrunk innermost first layer prior to the heat-shrinking of the outermost third layer to ensure the proper adherence of the filament layers to the innermost first layer.

Figure 12:
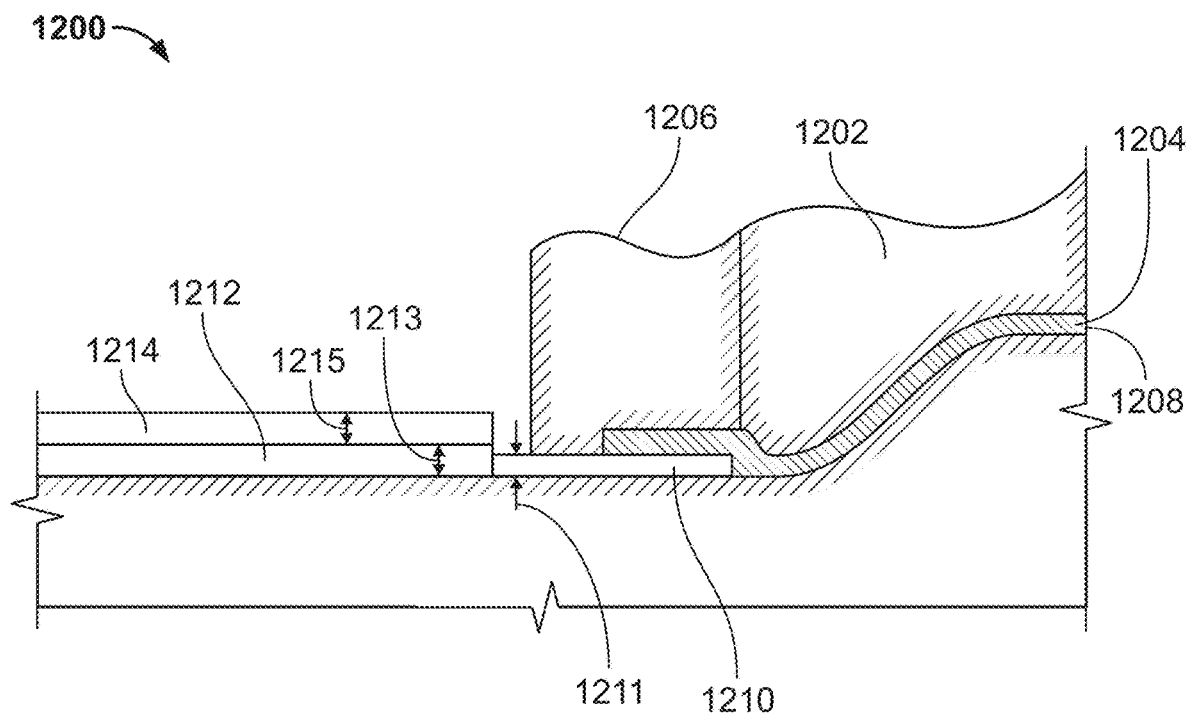
FIG. 12 shows a cross-section of the peel-away introducer sheath with mold tool on the break wall plane.
Figure 13:
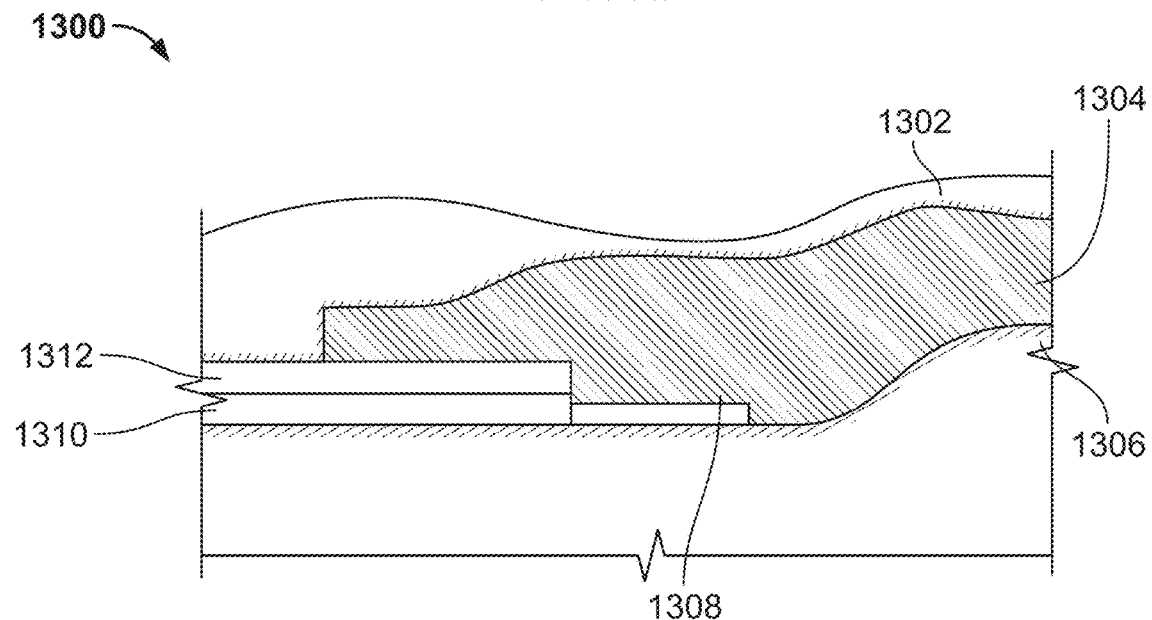
FIG. 13 shows a cross-section of the peel-away introducer sheath with the mold tool not on the break wall plane.

During removal of the sheath from the patient, the sheath hub is peeled away in addition to the sheath body. As described previously, and in relation to FIGS. 12 and 13, the sheath hub is manufactured using injection molding, in which the sheath hub material is placed into a sheath hub mold, the mold being configured with at least one insert. In some implementations, two inserts are used. After the sheath hub is molded and fused to the sheath body, the at least one insert is removed. As such, the sheath hub is configured during manufacturing to comprise a break wall in the form of negative space in the shape of the at least one. This negative space helps the practitioner to facilitate the peeling away of the sheath hub. FIG. 12 shows a cross-section 1200 of the introducer sheath with the mold tool on the break wall plane. The break wall is configured to have the shape of the two inserts upon their removal from the sheath hub material. In other configurations, one insert may be used, and in further implementations, more than two inserts may be used. Additionally, FIG. 12 shows reduced diameter section 1210. Reduced diameter section 1210 corresponds to a proximal segment along the sheath body which may only contain an inner layer, as the inner layer may be configured to extend further in a proximal direction than the reinforcing or outer layers. Reduced diameter section 1210 has a thickness 1211. Layer 1212 has thickness 1213 and layer 1214 has thickness 1215. In some implementations, thickness 1211 is less than the sum of thicknesses 1213 and 1215. In other implementations, thickness 1211 is equivalent to thickness 1213, such that reduced diameter section 1210 and layer 1212 form a single continuous layer. In other implementations, thickness 1211 is less than thickness 1213. As previously discussed, one advantage of the absence of a reinforcing layer in the proximal portion of the sheath is the stabilization the injection molding process, allowing the polymer layers of the sheath body to mold to the sheath hub with consistent properties. FIG. 13 shows a cross-section 100 of the introducer sheath with the mold tool not on the break wall plane, showing how the inserts are situated relative to the sheath hub.

Figure 11:
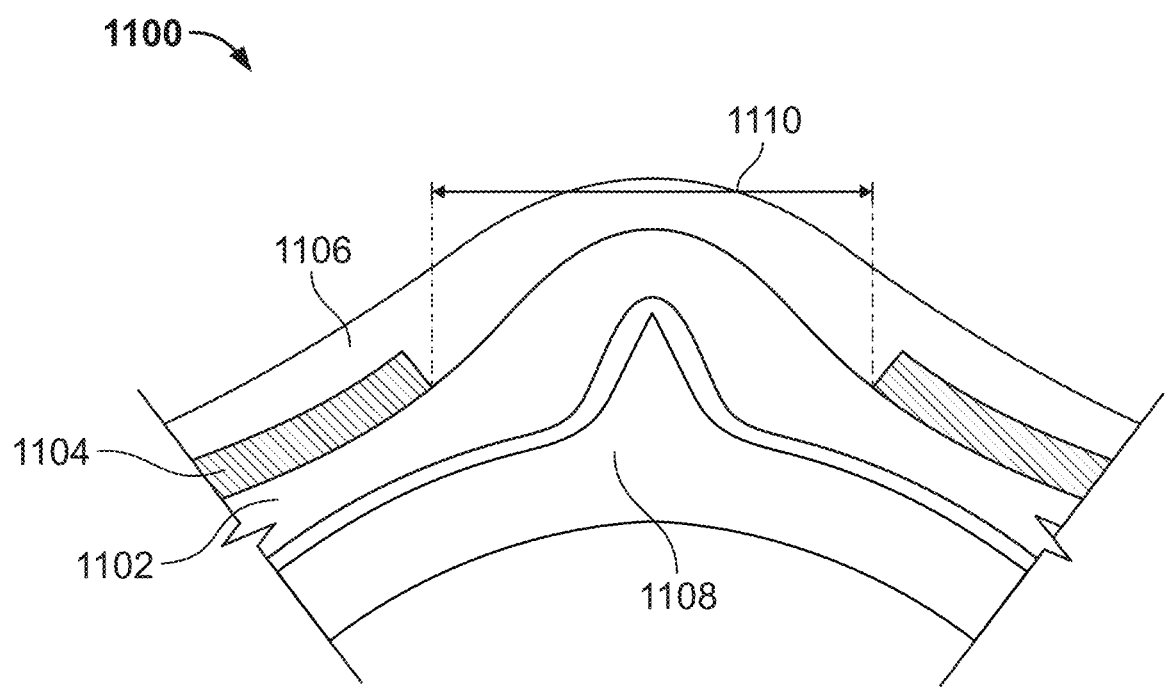
FIG. 11 shows a cross-section of the laser-cut hypotube with the internal notch in the circumferential discontinuity.

FIG. 11 shows a cross-section 1100 of a laser-cut hypotube 1104 with an internal notch 1108 in circumferential gap 1110. Inner layer 1102, reinforcing layer 1104, and outer layer 1106 are configured with the internal notch in the circumferential gap to increase peel-away functionality. As previously discussed, the discontinuity must be sufficiently large to allow for at least one inner or outer diameter notch to extend through it and to provide improved flexibility, but must also be sufficiently small to still provide improved kink resistance. In some implementations, the width of circumferential gap 1110 ranges between about 0.1 and about 1.5 millimeters. In other implementations, the width of circumferential gap 1110 ranges from about 0.3 to about 1.2 millimeters. In certain implementations, the width of critical gap 1110 ranges from about 0.5 to about 1.0 millimeters. In further implementations, the width of critical gap 1110 ranges from about 0.7 to about 0.8 millimeters. In certain implementations, the width of critical gap 1110 is about 0.761 millimeters.

Figure 14:
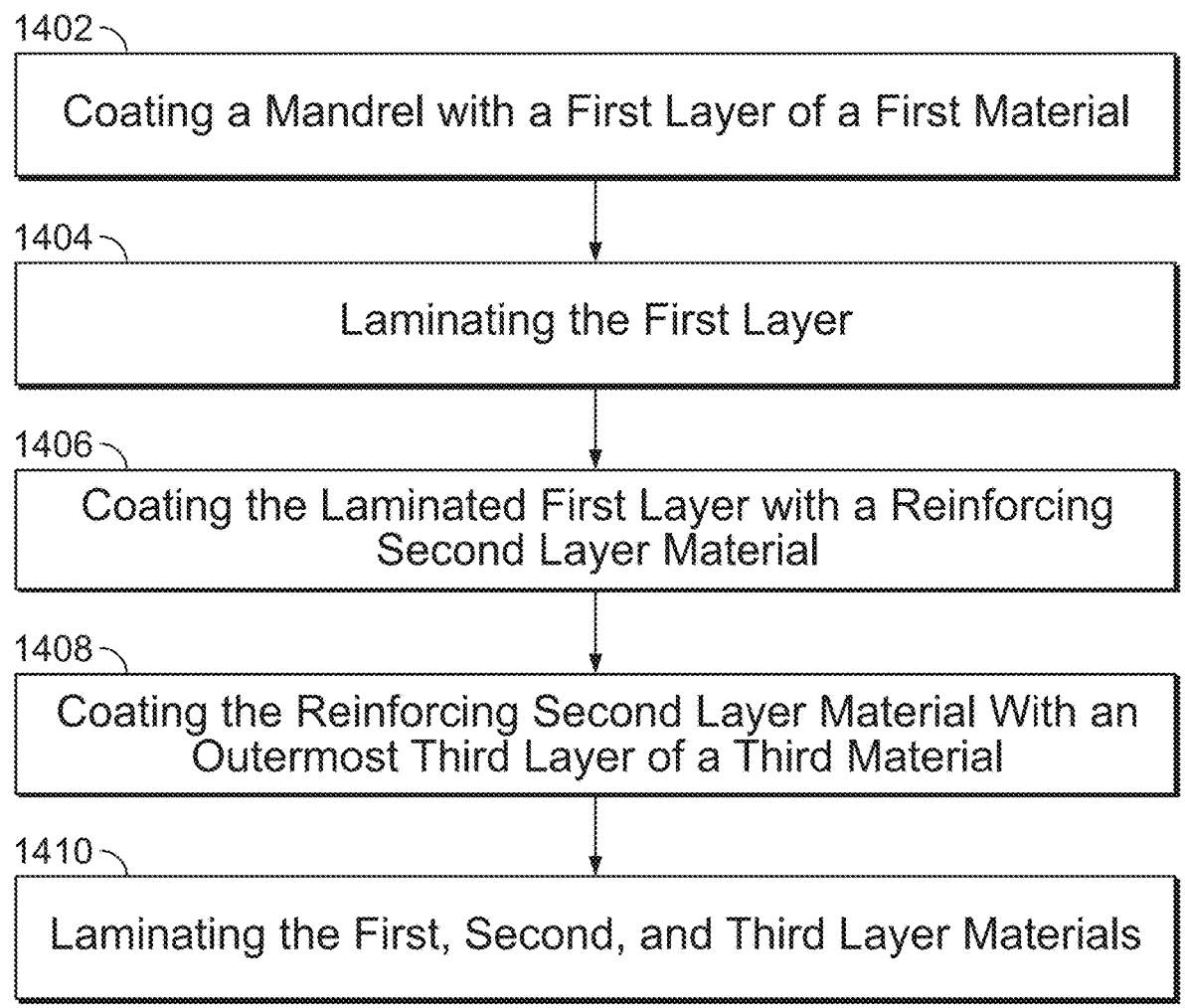
FIG. 14 shows an exemplary method of manufacturing certain implementations of a peel-away sheath assembly.

FIG. 14 shows a flowchart for manufacture of the peel-away sheath assembly for the introduction of a heart pump, according to certain implementations. Process 1400 begins at step 1402, wherein an operator coats a mandrel with a first layer of a first material. In some implementations, this first layer material is a thermoplastic, comprising one of PEBAX or TPU. In step 1404, the operator heat-shrinks the first layer, which comprises coating the first layer material with a heat shrink and heating the layer and the heat shrink. In step 1406, after the first layer is heat-shrunk, the operator coats the heat-shrunk first layer with a second layer of a reinforcing second layer material. In step 1408, the operator then coats the second layer of the reinforcing second layer material with an outermost layer of a third layer material. In step 1410, the operator heat-shrinks together the heat-shrunk first layer, the reinforcing second layer, and the third layer material. As previously discussed in relation to FIG. 3C, the openings in the reinforcing layer that form rings around the circumference of the reinforcing layer at regular longitudinal intervals along the length of the sheath body allow the inner and outer layers to reflow. This reflow provides better adherence of the inner and outer layers to each other, which allows the sheath body to better accommodate stresses while the sheath body is bent. The manufacturing process is controlled such that reflow of the inner and outer layers into the circumferential slits does not occur. The absence of the polymer layers from the slits allows the slits to serve as compression and expansion zones, providing the sheath body with improved flexibility. In further implementations of the method, the mandrel used in manufacture may possess at least one raised spine such that heat-shrinking of the first layer material leaves at least one internal notch in the heat-shrunk first layer. In other implementations, the operator selects the locations of each outer notch based on the geometry of the heat-shrunk reinforcing layer. In other implementations of the method, the operator need not subject the first layer to heat-shrinking prior to heat-shrinking the reinforcing second layer and the outermost third layer; that is, the operator may heat-shrink the first, second, and third layers for the first time simultaneously.

Figure 15:
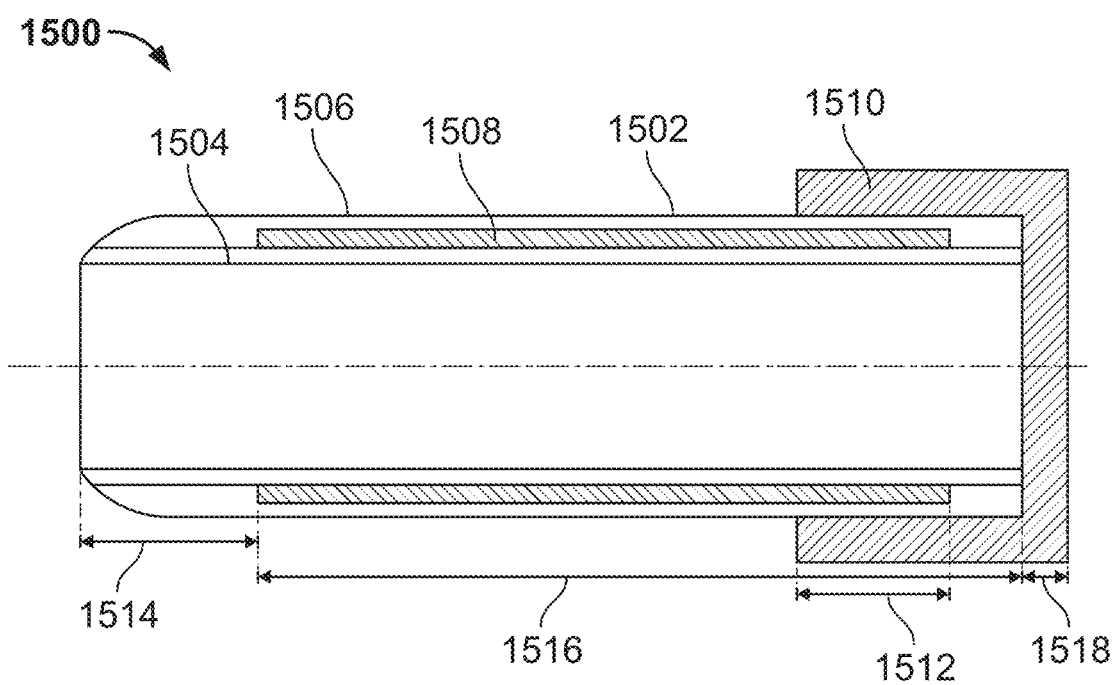
FIG. 15 shows an illustrative longitudinal cross-section of the peel-away introducer sheath with the reinforced layer extending into the peel-away sheath hub.

FIG. 15 shows a longitudinal cross-section 1500 of sheath body 1502 having inner layer 1504, outer layer 1506, reinforcing layer 1508, sheath hub 1510, reinforced hub length 1512, distal portion 1514, middle portion 1516, and proximal portion 1518. As discussed previously, the length of the sheath body 1502 through which reinforcing layer 1508 extends can be adjusted in order to prevent kinking along certain portions of sheath body 1502. For example, in some implementations, reinforcing layer 1508 is absent in distal portion 1514 while it is present in middle portion 1516. In such implementations, reinforcing layer 1508 may extend into proximal portion 1518 to a variable depth, as shown by reinforced hub length 1512. For example, the proximal end of reinforcing layer 1508 may terminate at the same longitudinal point at which sheath hub 1510 terminates. In other implementations, as shown in illustrative FIG. 15, reinforcing layer 1508 may terminate at a longitudinal point that is distal of the longitudinal point at which sheath hub 1510 terminates. In other implementations, the proximal end of reinforcing layer 1508 may terminate at a longitudinal point proximal of the longitudinal point at which sheath hub 1510 terminates. The longitudinal point at which reinforcing layer 1508 terminates may be given by reinforced hub length 1512. For example, reinforced hub length 1512 can extend into sheath hub 1510 to a desired depth in order to yield a desired kink resistance along a certain length of the sheath. Reinforced hub length 1512 may be, for example, two centimeters long, such that reinforcing layer 1508 terminates between 2 centimeters distal of the longitudinal point at which sheath hub 1510 terminates. In other implementations, reinforced hub length 1512 may be one centimeter, such that reinforcing layer 1508 terminates 1 centimeter distal the longitudinal point at which sheath hub 1510 terminates. In further implementations, reinforced hub length 1512 may be zero, such that reinforcing layer 1508 terminates at the longitudinal point at which sheath hub 1510 terminates. The specific distance between the point at which the reinforcing layer terminates and the point at which the sheath hub terminates can be selected to yield a specific kink resistance between those two points along the length of the sheath body. The surface of the reinforcing layer is configured with discontinuities to facilitate the peeling away of the reinforcing layer. The peeling away is initiated in the sheath hub, and for implementations having the reinforcing layer extend into the sheath hub, the peeling away of the reinforcing layer is facilitated, as the practitioner can directly apply the peel-away force to a portion of the sheath body containing the reinforcing layer.

Figure 16:
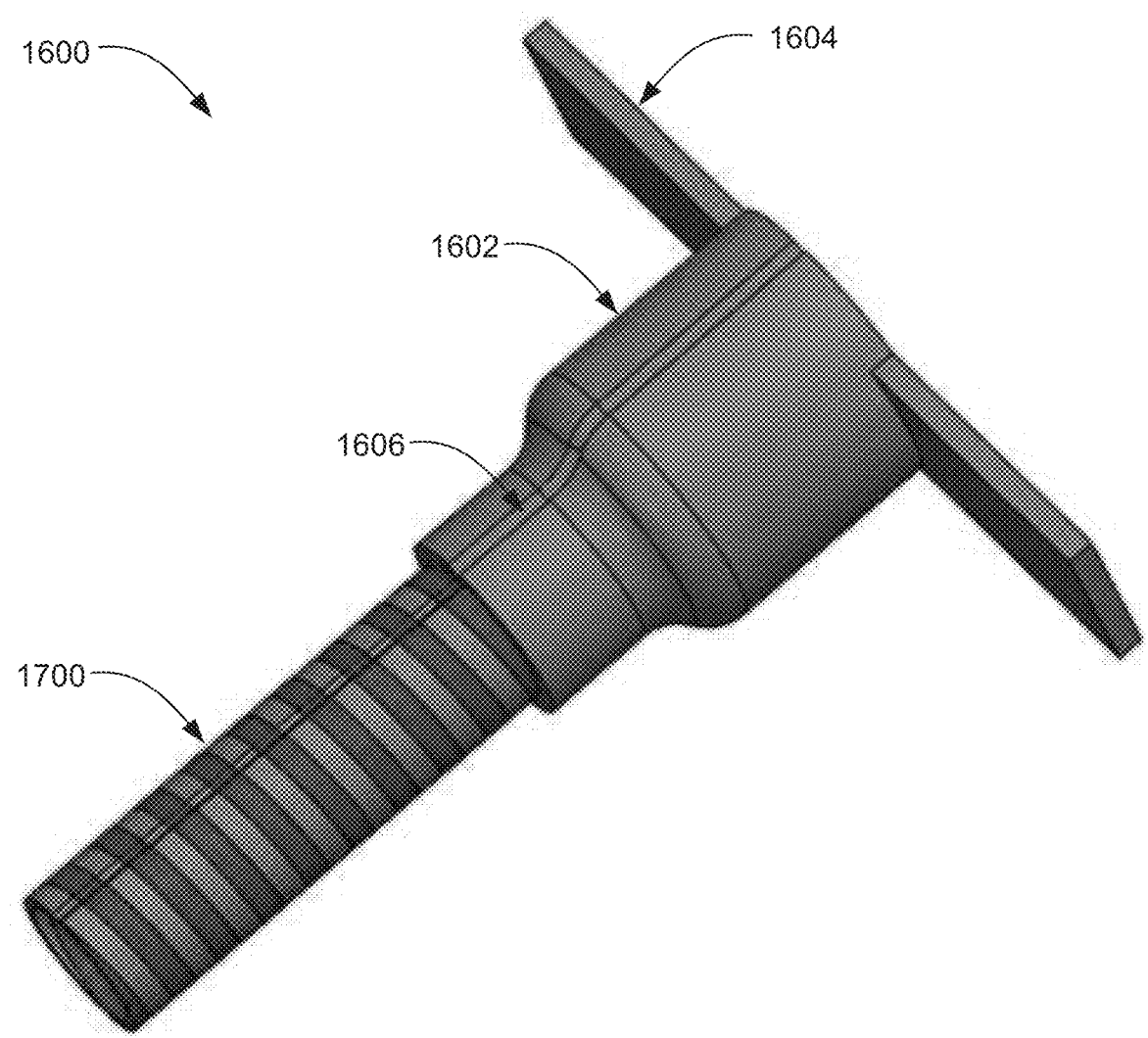
FIG. 16 shows an isometric view of an illustrative introducer sheath assembly including an illustrative expandable sheath body comprising two strips of material coupled to an illustrative sheath hub.
Figure 21:
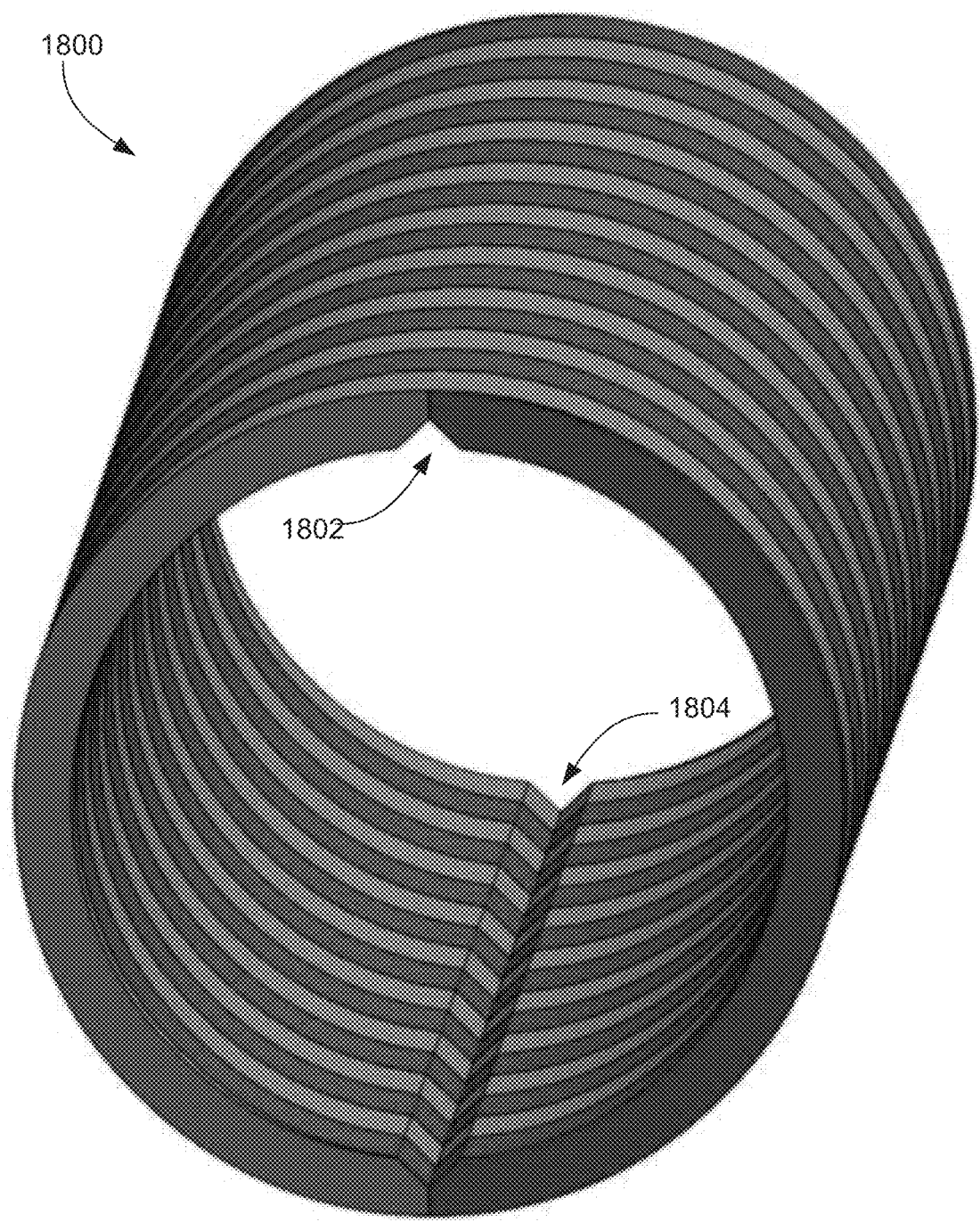
FIG. 21 shows an isometric view of the flexible sheath body of FIG. 20.
Figure 22:
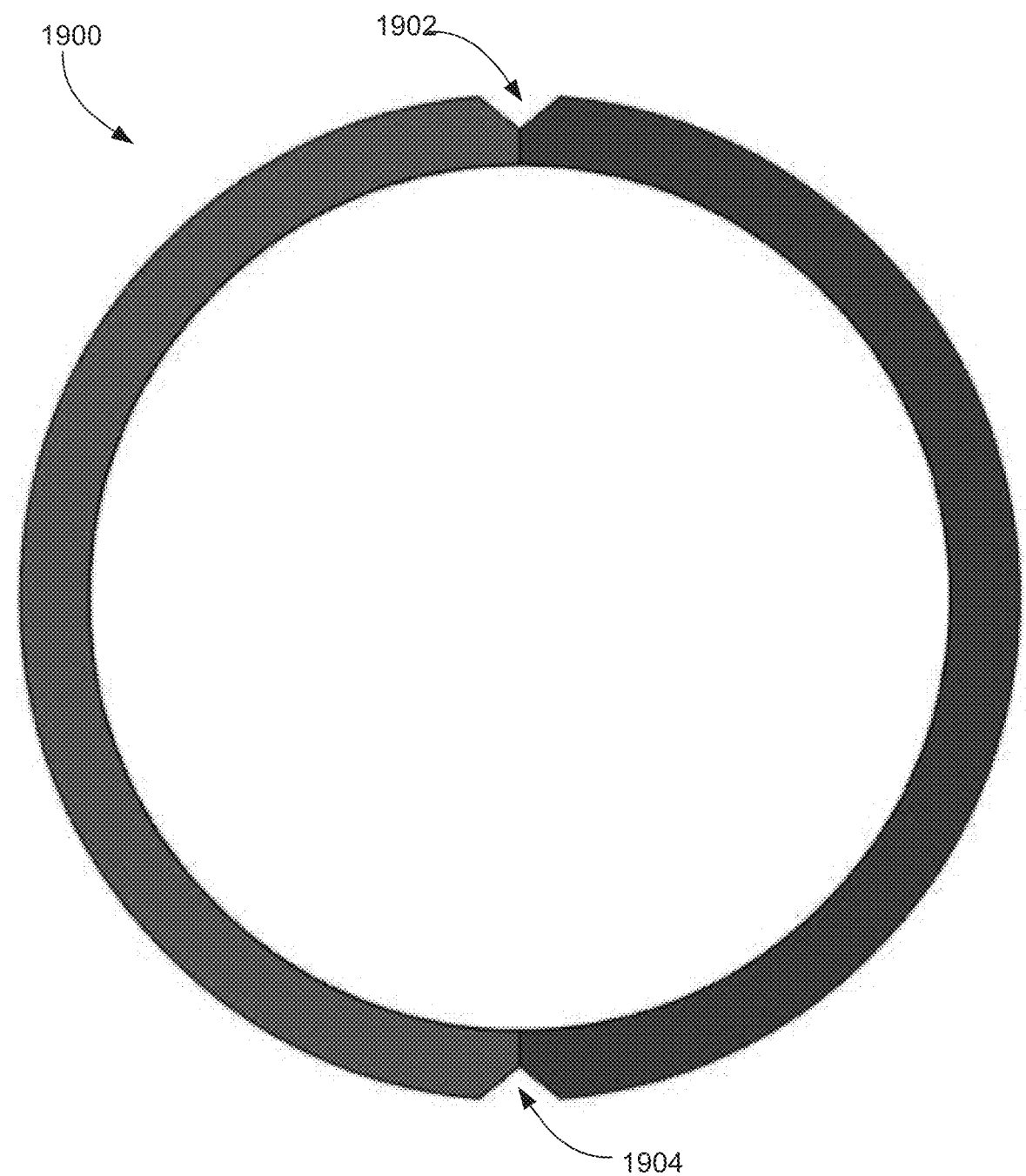
FIG. 22 shows a cross-sectional view of the flexible sheath body of FIG. 17 having the first notch and the second notch on an outer surface.
Figure 23:
FIG. 23 shows an isometric view of the flexible sheath of FIG. 22.

FIG. 16 shows an illustrative introducer sheath assembly 1600 including a sheath body 1700 (further described in relation to FIG. 17) coupled to a sheath hub 1602. As described further below in relation to FIGS. 17-19, the sheath body 1700 has a helical design including two strips 1706 and 1708 of materials with different rigidities. At least one benefit of this two-material helical design is the ability to obtain a sheath with composite material properties, to improve flexibility while improving kink resistance. In one aspect, the sheath body 1700 can have a ring design including alternating rings of materials with different rigidities. In another aspect, the sheath body 1700 can have a longitudinal strip design including alternating strips of materials with different rigidities. The sheath body 1700 and sheath hub 1602 both have proximal and distal ends. The distal end of the sheath hub 1602 is coupled to the proximal end of the sheath body 1700. For example, the distal end of the sheath hub is adhered or bonded to the proximal end of the sheath body. Alternatively, the distal end of the sheath hub is integrally formed with the proximal end of the sheath body. The sheath hub 1602 includes a gripping surface 1604 and notches 1606. The gripping surface 1604 may be formed of two diametrically opposed tabs, or any other suitable geometry for gripping. The gripping surface 1604 facilitates a peel-away of the sheath hub 1602 and the sheath body 1700. During peel-away of the sheath, a force is applied to the gripping surface 1604 (e.g. tabs as shown in FIG. 16) and the sheath hub 1602 is bisected along its longitudinal axis, beginning with notches 1606. Notches 1606 can be axially aligned along the length of the sheath hub and are oriented opposite each other. The notches 1606 on the sheath hub 1602 can be on an inner surface of the sheath hub 1602 or on an outside surface of the sheath hub 1602. The sheath hub 1602 can be separated into two pieces by breaking the sheath hub along the notches 1606 through the application of force to the gripping surface 1604 of the sheath hub 1602. As described further below in relation to FIGS. 20-23, the sheath body can have notches on an inside surface of the sheath body 1700 (FIGS. 20 and 21) or on an outside surface of the sheath body 1700 (FIGS. 22 and 23). Notches along the sheath body 1700 may be replaced by score lines. The notches on sheath body 1700 can align with notches 1606 in order to facilitate the peel-away of the sheath hub 1602 and the sheath body 1700. At least one advantages of the notches or score lines on sheath body 1700 is improving the ease with which the sheath may be peeled-away, cutting across both helical strips of the sheath. The sheath body 1700 can be separated into two pieces after breaking the sheath hub 1602 by breaking the sheath body 1700 along the notches of the sheath body 1700 through further application of force to the gripping surface 1604 of the sheath hub 1602.

The lumens of the sheath body 1700 and sheath hub 1602 are in fluid communication, allowing for passage of a medical device between the sheath hub 1602 and the sheath body 1700. In one aspect, the sheath hub 1602 includes a hemostasis valve. The hemostasis valve can be sized to prevent fluid from exiting the proximal end of the hub during the insertion of a medical device.

Figure 17:
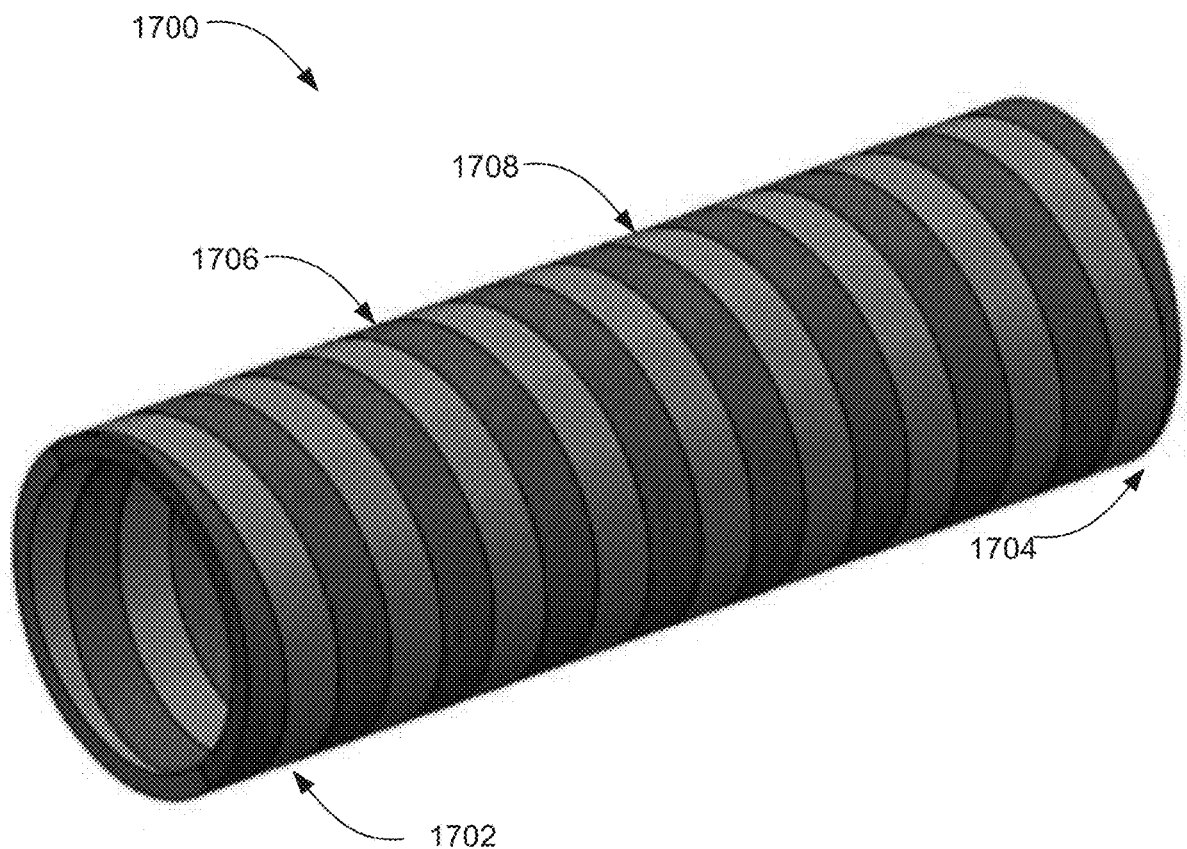
FIG. 17 shows an isometric view of an illustrative flexible sheath body having a first strip and a second strip.
Figure 18:
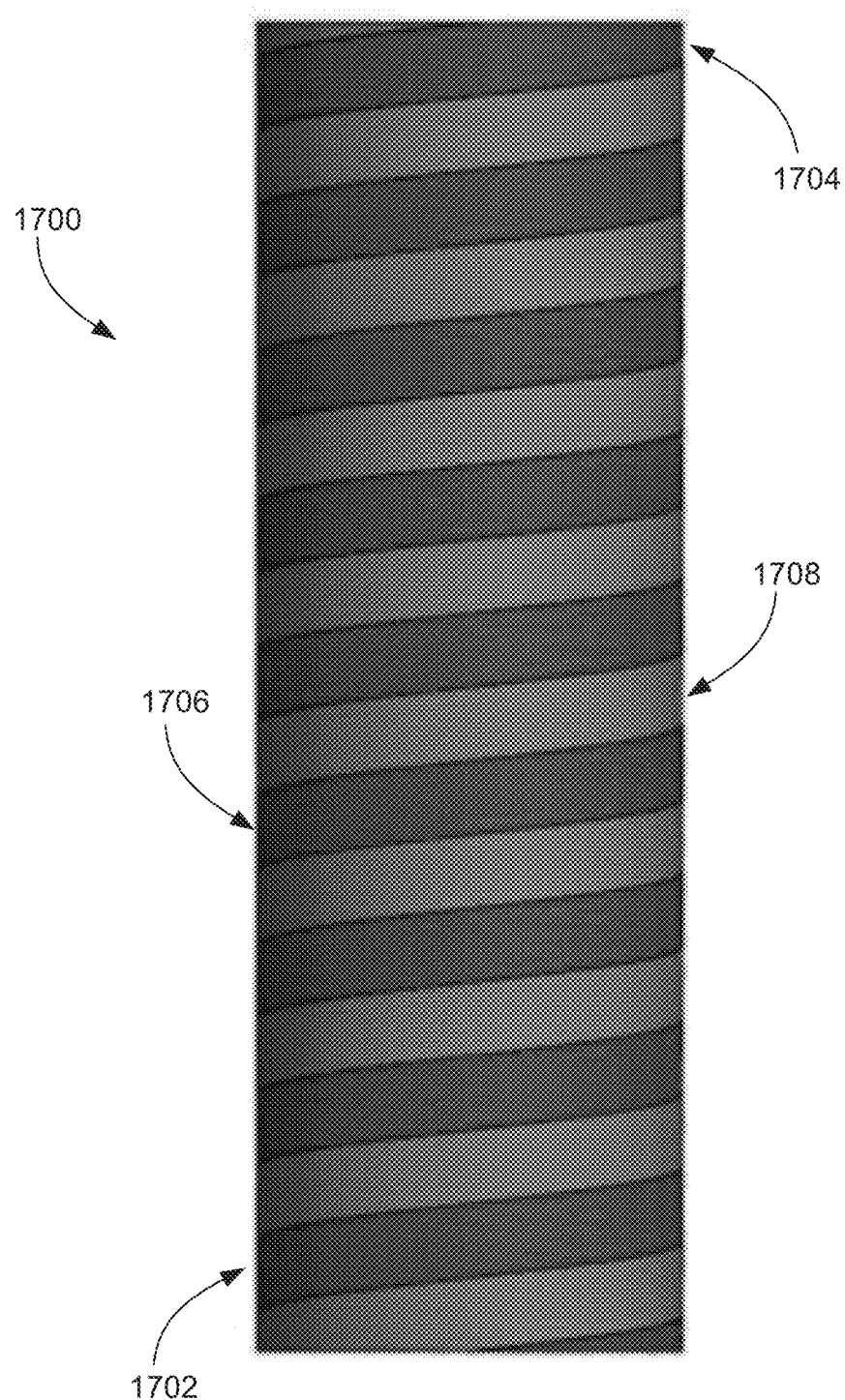
FIG. 18 shows an illustrative view of the flexible sheath body of FIG. 17.

FIGS. 17 and 18 show an illustrative sheath body 1700 (e.g. the sheath body 1700 of FIG. 16), comprising a distal end 1702, a proximal end 1704, a first strip 1706, and a second strip 1708. The first strip 1706 and the second strip 1708 are oriented in alternating or complementary helices extending from the distal end 1702 to the proximal end 1704 of the sheath body 1700, forming a cylindrical lumen. As described further below in relation to FIG. 19, the inner diameter of the lumen, the widths of the first strip 1706 and the second strip 1708, and the helix angle are correlated and the corresponding values selected to obtain the desired sheath properties. The lumen can be sized to allow for the insertion of a medical device. For example, the lumen can be sized to allow for the insertion of a percutaneous pump. The inner diameter of the lumen can range from 3 Fr (1 mm) to 23 Fr (7.67 mm). The length of the sheath body 1700 can range from 7 cm (e.g. for percutaneous axillary/sub-clavian insertions) to 45 cm (e.g. for femoral transcaval insertions). For percutaneous access through the axillary/subclavian arteries the length of the sheath body can be shorter. In contrast, for percutaneous access through the femoral artery, a longer sheath body is needed.

The first strip 1706 and the second strip 1708 are made of materials having different flexibility and rigidity. For example, the first strip 1706 is made of a first material having a first rigidity and the second material is made of a second material having a second rigidity. The first rigidity can be larger than the second rigidity. Examples of materials that can be used as the first and second materials include polyether block amide (PEBA) materials, polyethylene materials, and thermoplastic elastomers. Examples of PEBA materials that can be used as the first and second materials include PEBAX 7233 and PEBEX 3533, respectively. Low-density polyethylene (LDPE) and high-density polyethylene (HDPE) are examples of polyethylene materials that can be used as the first material. Examples of thermoplastic elastomers that can be used as the second material include styrene ethylene butylene styrene (SEB S) and ethylene-vinyl acetate (EVA). For example, the first strip 206 can be made of PEBAX 7233 while the second strip 1708 is made of EVA. At least one benefit of having the first strip juxtaposed with the second strip having different material properties is the ability to select specific rigidity properties for the introducer sheath as a whole.

The distal end 1702 of the sheath body 1700 can include a tapered tip. The tapered tip maintains a constant inner diameter of the lumen of the sheath body 1700 but tapers the outside wall of the sheath body 1700 in order to allow for a smooth transition at the distal end 1702 of the sheath body 1700. The tapered tip can be formed from the first material of the first strip 1706, the second material of the second strip 1708, both the first material and the second material, or a third material. If the tapered tip is formed from both the first material and the second material, the tapered tip can be manufactured through thermoforming the sheath body 1700 in a die. If the tapered tip is formed from the first material only, the second material only, or a third material only, the tapered tip can be manufactured through thermoforming a small tube of the selected tapered tip material onto the distal end 1702 of the sheath body 1700. At least one advantage of the tapered tip is to minimize trauma to the vasculature when inserting the sheath, while maintaining the desired material properties for the sheath.

Figure 19:
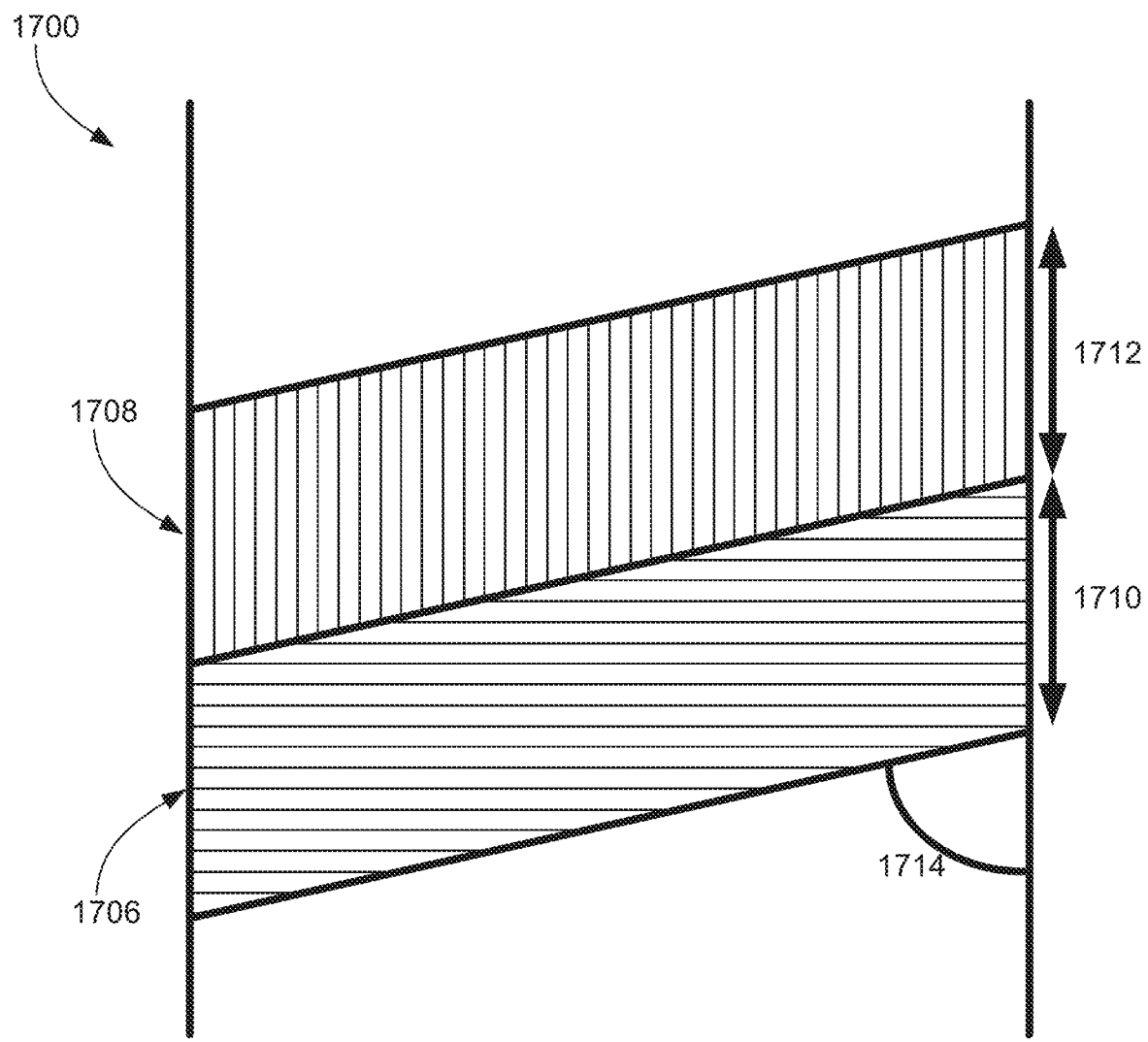
FIG. 19 shows a schematic profile of the flexible sheath body of FIG. 17 with the first strip and the second strip having widths and a helix angle.

FIG. 19 shows a schematic profile of the flexible sheath body 1700 of FIG. 17 with the first strip 1706 having a first width 1710 and the second strip 1708 having a second width 1712. Also shown in FIG. 19 is helix angle 1714. Helix angle 1714 is defined as the arctangent of the ratio of the inner diameter of the lumen of the sheath body 1700 to the thicker of first width 1710 and second width 1712. The first width 1710 and second width 1712 can range from 0.17 mm to 3.83 mm. In one aspect, the first width 1710 and the second width 1712 can be the same width. For example, the first width 1710 and the second width 1712 can be 1 mm. In another aspect, the first width 1710 and the second width 1712 can be different widths. For example, the first width 1710 can be 3 mm and the second width can be 1 mm. The helix angle can vary from 0° to 90°. In the helix design, the helix angle 1714 preferably ranges from 60° to 80°. As mentioned above, the sheath body 1700 can alternatively have a ring design including alternating rings of materials with different rigidities or a longitudinal strip design including alternating strips of materials with different rigidities. If using a ring design, the helix angle 1714 is 90° because each ring is perpendicular with the lumen of the sheath body 1700. If using a longitudinal strip design, the helix angle 1714 is 0° because each strip is parallel with the lumen of the sheath body 1700.

Figure 20:
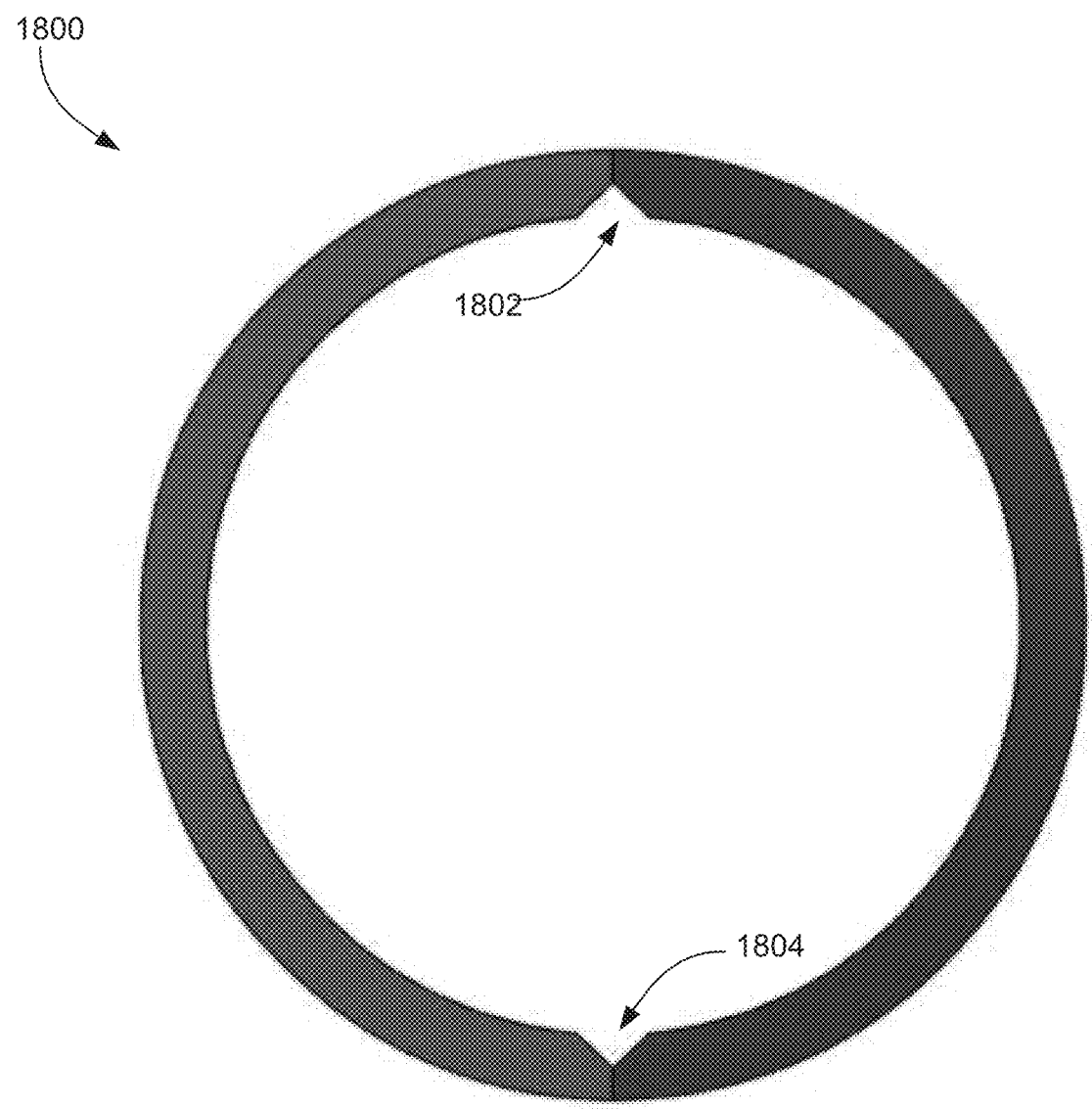
FIG. 20 shows a cross-sectional view of the flexible sheath body of FIG. 17 having a first notch and a second notch on an inner surface.

As mentioned above, sheath body 1700 can have notches that facilitate a peel away of the sheath body 1700. The notches can be triangular in shape and form a part of a wall of the sheath body 1700. The wall of the sheath body 1700 can range in thickness from 0.1 mm to 1.67 mm. The notches can take up 50% to 90% of the total wall thickness. For example, the thickness of the notches can be between 0.05 mm and 1.5 mm. FIGS. 20 and 21 show an illustrative sheath body 1800 comprising a first inner notch 1802 and a second inner notch 1804. The first inner notch 1802 and second inner notch 1804 can be axially aligned along the length of the sheath body 1800 and oriented opposite each other. The first inner notch 1802 and the second inner notch 1804 run along the inner surface of the sheath body 1800. As described further below in relation to FIG. 9, the first inner notch 1802 and the second inner notch 1804 can be formed on a mandrel during the manufacturing of the sheath body 1800. Similarly, the inner notches 1606 of the sheath hub 1602 can be formed on a core pin during the manufacturing of the sheath hub 1602. Putting notches on the inner surface of the sheath body helps maintain a smooth circular outer profile of the sheath body while enabling an easier peeling-away of the sheath, cutting across the helices of the first strip 1706 and second strip 1708.

Alternatively, the notches on the sheath body can be on the outer surface of the sheath body. FIGS. 22 and 23 show an illustrative sheath body 1900 comprising a first outer notch 1902 and a second outer notch 1904. The first outer notch 1902 and second outer notch 1904 can be axially aligned along the length of the sheath body 1900 and oriented opposite each other. The first outer notch 1902 and the second outer notch 1904 can be cut out of the sheath body 1900 by skiving. Similarly, the outer notches 1606 of the sheath hub 1602 can be cut out of the sheath hub 1602, at least partially, by skiving. In another aspect, the outer notches 1606 of the sheath hub 1602 can be formed with a geometry in a mold during the manufacturing the of the sheath hub 1602. Putting the notches on the outer surface of the sheath provides a smooth circular inner surface of the sheath to facilitate passage of instruments and a device for insertion.

Figure 24:
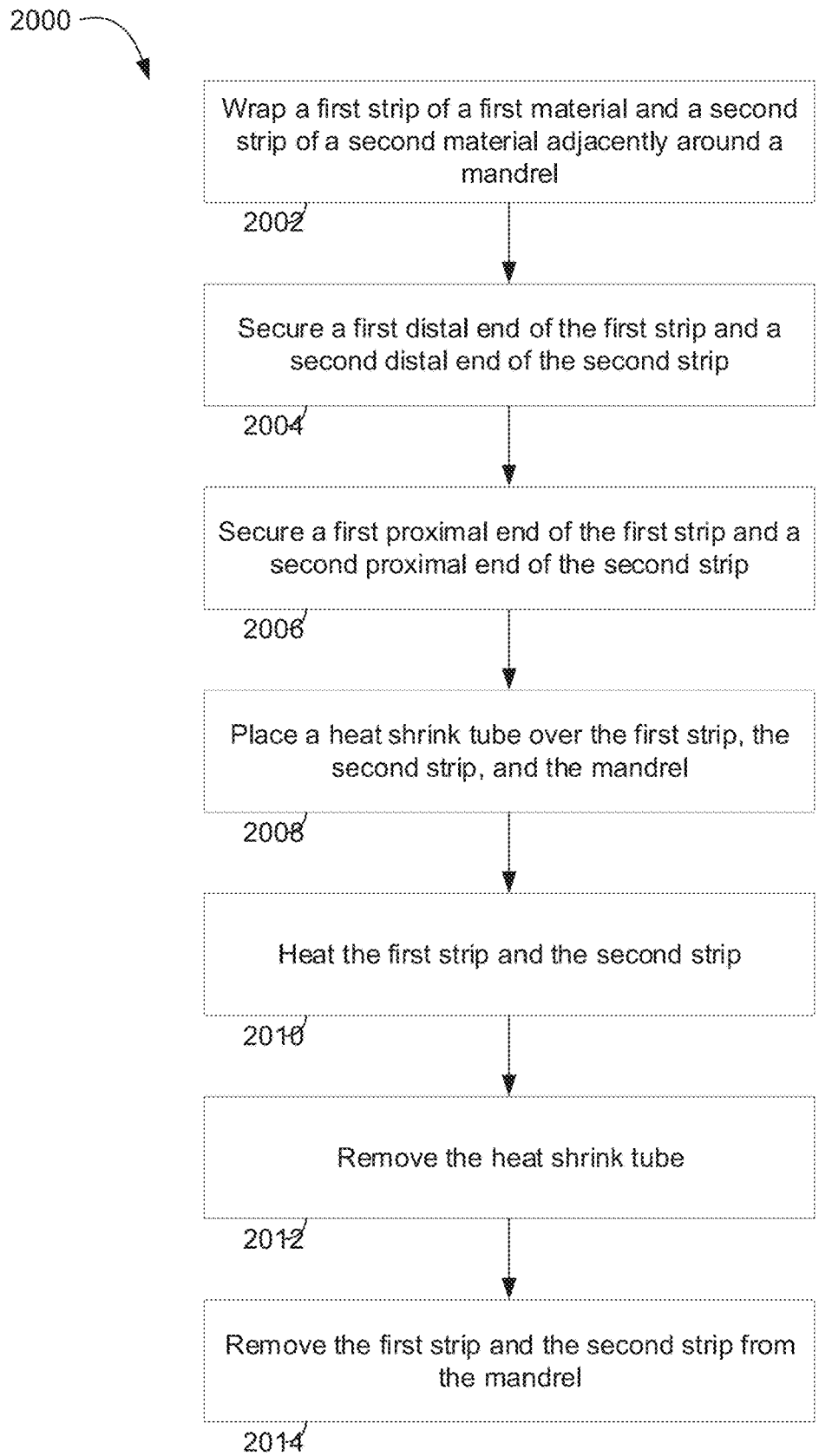
FIG. 24 shows an illustrative method for manufacturing the flexible sheath body of FIG. 17.

The sheath body 1700 can be made using a lamination process whereby the first strip 1706 and the second strip 1708 are wrapped around a lamination mandrel and heated to bond together. FIG. 24 shows a process 1900 of manufacturing the flexible sheath body 1700, described above in relation to FIG. 17, by lamination. At step 1702, a first strip 1706 of a first material and a second strip 1708 of a second material are wrapped adjacently around a mandrel. As mentioned above in relation to FIG. 17, the first strip 1706 and the second strip 1708 can be made of materials having different flexibility and rigidity. For example, the first strip 1706 can be made of a first material having a first rigidity and the second material can be made of a second material having a second rigidity. The first rigidity can be larger than the second rigidity.

At step 1904, a first distal end of the first strip 1706 and a second distal end of the second strip 1708 is secured. For example, the first distal end of the first strip 1706 and the second distal end of the second strip 1708 can be pinched in place against the mandrel. Alternatively, both distal ends can be entrapped within a restraining sheath, or held in place by a temporary adhesive.

At step 1906, a first proximal end of the first strip 1706 and a second proximal end of the second strip 1708 is secured. Any of the methods used to secure the distal ends of the strips 1706 and 1708 can be used to secure the proximal ends of the strips 1706 and 1708.

At step 1908, a heat shrink tube is placed over the first strip 1706, the second strip 1708, and the mandrel. Heat is applied over the heat shrink tube, which heats the first strip 1706 and the second strip 1708 and bonds them to each other along the helical edges of each strip. The heat shrink tube can be made of a polytetrafluoroethylene (PTFE) material, a fluorinated ethylene propylene (FEP), or other suitable heat shrink material. The source of energy used to apply heat over the heat shrink tube can be a laser beam or any other suitable heat generating method.

At step 1910, the heat shrink tube, first strip 1706, and second strip 1708 are heated. During the heating, the heat shrink tube material remains intact (i.e. does not melt) whereas first strip 1706 and second strip 1708 are reflowed and bonded together along the helical edges of each strip.

At step 1912, the heat shrink tube is removed, leaving the bonded first strip 1706 and the second strip 1708 on the mandrel.

At step 1914, the sheath body 1700, formed by the bonded first strip 1706 and second strip 1708, is removed from the mandrel. For example, when the bonded strips may be removed as a whole from the mandrel may depend on a length of time needed for the bonded strips to cool down after the heat-shrink process is complete. As mentioned above in relation to FIGS. 19 and 20, the mandrel can include protrusions with triangular geometries, which can mold inner notches 1802 and 1804 onto the sheath body 1700. The triangular geometries on the mandrel can be axially aligned along the length of the mandrel and oriented opposite each other. The triangular geometries on the mandrel can have the dimension of the desired inner notches 1802 and 1804. For example, the height of the triangular geometries on the mandrel can range from 0.05 mm up to 1.5 mm. At least one advantage of the manufacturing method described above includes the ability to obtain a sheath with evenly bonded strips of two different materials, in order to obtain a sheath with composite material properties having improved flexibility and kink-resistance for introducing the sheath into a patient vasculature.

Figure 25:
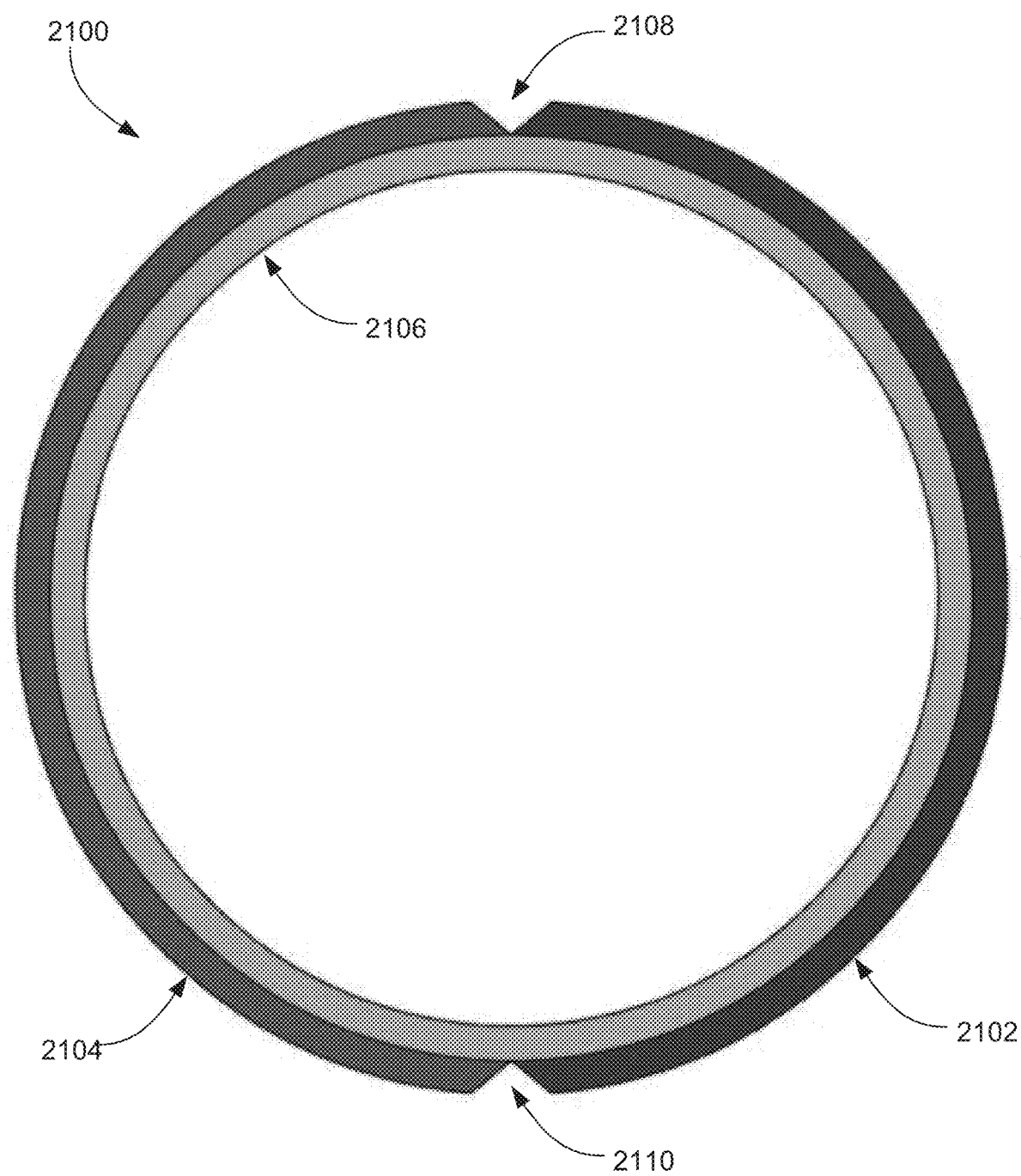
FIG. 25 shows a cross-sectional view of a flexible sheath body having an inner lumen and a first notch and a second notch on an outer surface.

As mentioned above, the sheath body can be made from two strips of materials having different rigidity. Alternatively, the sheath body can include an inner lumen made of a third material. FIG. 25 shows an illustrative sheath body 2100 comprising a first strip made of a first material 2102, a second strip made of a second material 2104, and an inner lumen 2106. In one aspect, sheath body 2100 comprises a ring design including alternating rings of materials having different rigidities. In another aspect, sheath body 2100 comprises a longitudinal strip design including alternating strips of materials having different rigidities. The inner lumen 2106 can be made of a third material having the same or different rigidity as the first and/or second materials. In one aspect, the inner lumen 2106 can be made with the same material as the first strip 2102 or the second strip 2104. In another aspect, the inner lumen 2106 can be made from a lubricious material such as PTFE or FEP. Similar to sheath body 1800 discussed in relation to FIGS. 20 and 21, sheath body 2100 includes first outer notch 2108 and a second outer notch 2110. The first outer notch 2108 and second outer notch 2110 can be axially aligned along the length of the sheath body 2100 and oriented opposite each other. The first outer notch 2108 and second outer notch 2110 can go through the thickness of the first strip 2102 and the second strip 2104. Alternatively, the first outer notch 2108 and second outer notch 2110 can go through the thickness of the first strip 2102 and the second strip 2104 as well as continue partially but not completely through the thickness of the inner lumen 2106. As mentioned above, the first outer notch 2108 and the second outer notch 2110 can be cut out of the sheath body 2100 by skiving. As discussed in relation to FIGS. 20 and 21, the notches can alternatively be on the inner surface such that the first strip 2102 and the second strip 2104 are surrounded by an outer tube. By including inner lumen 2106 in sheath body 2100, a consistent and smooth tear propagation can be achieved compared with sheath bodies 1700, 1800, and 1900. Having the first outer notch 2108 and second outer notch 2110 partially extend through the thickness of the inner lumen 2106 increases the likelihood that the tear propagates along the notches and decreases the likelihood that the tear propagates along the interface between the first strip and the second strip.

The foregoing is merely illustrative of the principles of the disclosure and the apparatuses can be practiced by other than the described aspects, which are presented for purposes of illustration and not of limitation. It is to be understood that the apparatuses disclosed herein, while shown for use in percutaneous insertion of blood pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions and alterations are ascertainable by one skilled in the art and could be made without departing from the scope of the information disclosed herein. All references cited herein are incorporated by reference in their entirety and made part of this application.

The invention claimed is:

1. A peel-away sheath assembly for insertion of a blood pump, the peel-away sheath assembly comprising:
   a peel-away sheath hub comprising at least one circumferential discontinuity; and
   a peel-away sheath body comprising:
      a proximal end connected to the peel-away sheath hub,
      a distal end,
      an outer layer defining an outer radius of the peel-away sheath body and defining an outermost surface,
      an inner layer defining a first lumen of the peel-away sheath body with an inner radius and defining an innermost surface, and
      a reinforcing layer located between the inner radius and the outer radius,
      wherein the reinforcing layer has a rigidity that is greater than at least one of a rigidity of the inner layer or a rigidity of the outer layer of the sheath body;
      one or more notches extending from at least one of the outermost surface or the innermost surface, or both the outermost surface and the innermost surface, of the peel-away sheath body and through the outer layer and the reinforcing layer or through the inner layer and the reinforcing layer, or both through the outer layer and the reinforcing layer and through the inner layer and the reinforcing layer, respectively,
      wherein the one or more notches are configured as a succession of aligned discrete notches or as a continuous notch, the one or more notches defining at least one peel-away line along a length of the peel-away sheath body, the at least one peel-away line being aligned with the one or more notches, wherein the peel-away sheath body is configured to be peeled away along the at least one peel-away line; and
   wherein the at least one circumferential discontinuity of the hub is aligned with at least one notch of the one or more notches of the peel-away sheath body and wherein the at least one circumferential discontinuity of the hub provides a reduced thickness portion of the peel-away sheath hub.

2. The peel-away sheath assembly of claim 1, wherein the reinforcing layer is a hypotube.

3. The peel-away sheath assembly of claim 1, wherein the one or more notches include two notches defining the at least one peel-away line including first and second peel-away lines on the innermost surface or the outermost surface of the peel-away sheath body, wherein at any longitudinal location along the peel-away sheath body, a first notch axis is at a same circumferential location as the first peel-away line and a second notch axis is at a same circumferential location as the second peel-away line.

4. The peel-away sheath assembly of claim 3, wherein at least one of the first and second peel-away lines is located on the innermost surface of the peel-away sheath body.

5. The peel-away sheath assembly of claim 3, wherein at least one of the first and second peel-away lines is located on the outermost surface of the peel-away sheath body.

6. The peel-away sheath assembly of claim 3, wherein the first and second peel-away lines are diametrically opposed from one another.

7. The peel-away sheath assembly of claim 3, the peel-away sheath hub further comprising:
- a proximal conical portion, and
- a distal cylindrical portion, wherein the reduced thickness portion of the peel-away sheath hub provided by the at least one circumferential discontinuity is in the proximal conical portion.

8. The peel-away sheath assembly of claim 7, wherein the at least one circumferential discontinuity of the sheath hub is a first circumferential discontinuity and a second circumferential discontinuity, wherein the proximal conical portion comprises the first circumferential discontinuity, and wherein the distal cylindrical portion comprises the second circumferential discontinuity.

9. The peel-away sheath assembly of claim 8, wherein the first circumferential discontinuity and the second circumferential discontinuity are aligned in a longitudinal direction and together define a peel-away line.

10. The peel-away sheath assembly of claim 9, wherein a distal end of the second circumferential discontinuity abuts a proximal end of at least one of the first and second peel-away lines on the innermost surface or the outermost surface of the peel-away sheath body.

11. The peel-away sheath assembly of claim 10, wherein the inner layer and the outer layer comprise a thermoplastic.

12. The peel-away sheath assembly of claim 3, wherein the reinforcing layer is present only in a middle portion of the peel-away sheath body.

\* \* \* \* \*

UNITED STATES PATENT AND TRADEMARK OFFICE
CERTIFICATE OF CORRECTION

PATENT NO. : 11,793,977 B2
APPLICATION NO. : 16/414474
DATED : October 24, 2023
INVENTOR(S) : Christopher Nason Korkuch et al.

It is certified that error appears in the above-identified patent and that said Letters Patent is hereby corrected as shown below:

In the Specification

Column 19, Line 22:
Now reads: "224204"; should read -- 204 --

Column 19, Line 23:
Now reads: "226206"; should read -- 206 --

Column 25, Line 48:
Now reads: "100"; should read -- 1300 --

Column 28, Line 53:
Now reads: "(SEB S)"; should read -- (SEBS) --

Column 28, Line 54:
Now reads: "206"; should read -- 1706 --

Column 30, Line 14:
Now reads: "1900"; should read -- 2000 --

Column 30, Line 16:
Now reads: "1702,"; should read -- 2002, --

Column 30, Line 26:
Now reads: "1904"; should read -- 2004 --

Column 30, Line 33:
Now reads: "1906"; should read -- 2006 --

Signed and Sealed this
Twenty-third Day of January, 2024

Katherine Kelly Vidal
*Director of the United States Patent and Trademark Office*

Column 30, Line 33:
Now reads: "1906,"; should read -- 2006, --

Column 30, Line 38:
Now reads: "1908,"; should read -- 2008, --

Column 30, Line 48:
Now reads: "1910,"; should read -- 2010, --

Column 30, Line 53:
Now reads: "1912,"; should read -- 2012, --

Column 30, Line 56:
Now reads: "1914,"; should read -- 2014, --